(12) United States Patent
Murphy et al.

(10) Patent No.: US 10,758,579 B2
(45) Date of Patent: Sep. 1, 2020

(54) SYSTEMS AND METHODS FOR EXTRACTION OF NATURAL PRODUCTS

(71) Applicant: METAGREEN VENTURES, Los Angeles, CA (US)

(72) Inventors: Randall B. Murphy, Glenmoore, PA (US); Loren Erik Snyder, Streetsboro, OH (US)

(73) Assignee: METAGREEN VENTURES, Los Angeles, CA (US)

( * ) Notice: Subject to any disclaimer, the term of this patent is extended or adjusted under 35 U.S.C. 154(b) by 523 days.

(21) Appl. No.: 15/469,311

(22) Filed: Mar. 24, 2017

(65) Prior Publication Data

US 2018/0153948 A1  Jun. 7, 2018

Related U.S. Application Data

(60) Provisional application No. 62/431,351, filed on Dec. 7, 2016.

(51) Int. Cl.
| | | |
|---|---|---|
| *A61K 36/185* | (2006.01) | |
| *A61K 31/352* | (2006.01) | |
| *B01D 11/02* | (2006.01) | |

(52) U.S. Cl.
CPC .......... *A61K 36/185* (2013.01); *A61K 31/352* (2013.01); *B01D 11/0288* (2013.01); *A61K 2236/333* (2013.01); *A61K 2236/37* (2013.01)

(58) Field of Classification Search
CPC .......... A61K 2236/333; A61K 2236/37; A61K 31/352; A61K 36/185; B01D 11/0288
See application file for complete search history.

(56) References Cited

U.S. PATENT DOCUMENTS

| | | | |
|---|---|---|---|
| 2,294,811 A | 9/1942 | Stoll et al. | |
| 2,410,101 A | 10/1946 | Park et al. | |
| 2,449,671 A | 9/1948 | Rhodes | |
| 2,467,403 A | 4/1949 | Pascal | |
| 2,472,121 A | 6/1949 | Omfelt | |
| 3,150,050 A | 9/1964 | Safrin et al. | |
| 3,669,679 A | 6/1972 | Panzer et al. | |
| 4,490,398 A | 12/1984 | Behr et al. | |
| 4,818,533 A | 4/1989 | Boulware et al. | |
| 4,820,537 A | 4/1989 | Katz | |
| 4,996,317 A | 2/1991 | O'Brien et al. | |
| 5,288,511 A | 2/1994 | Kazlas et al. | |
| 5,405,633 A | 4/1995 | Heidlas et al. | |
| 6,455,087 B1 | 9/2002 | Nicola | |
| 6,649,205 B2 | 11/2003 | Nicola | |
| 6,746,695 B1 | 6/2004 | Martin et al. | |
| 6,890,424 B1 * | 5/2005 | Wilde | B01D 11/0219 208/311 |
| 8,119,697 B2 | 2/2012 | Mechoulam et al. | |
| 2001/0021367 A1 * | 9/2001 | Powell | A01N 63/00 423/658.5 |
| 2006/0182689 A1 | 8/2006 | Dournel et al. | |
| 2007/0110835 A1 | 5/2007 | Maes et al. | |
| 2008/0103193 A1 | 5/2008 | Castor et al. | |
| 2008/0194779 A1 * | 8/2008 | Christmas | B01J 23/18 526/75 |
| 2008/0300386 A1 | 12/2008 | Lazarev et al. | |
| 2009/0286301 A1 | 11/2009 | Tao et al. | |
| 2010/0087518 A1 | 4/2010 | Bhatarah et al. | |
| 2010/0314240 A1 | 12/2010 | Lin et al. | |

FOREIGN PATENT DOCUMENTS

| | | |
|---|---|---|
| EP | 0711508 A1 | 5/1996 |
| WO | 0064555 A2 | 11/2000 |
| WO | 2018106973 A1 | 6/2018 |

OTHER PUBLICATIONS

Noles JR; Zollweg JA "Vapor-Liquid Equilibrium for Chlorodifluoromethane+Dimethyl Ether from 283 to 395 K at pressues to 5 MPa" J. Chem. Eng. Data, 37(3), pp. 306-310. (Year: 1992).*
Byun H-S, et al "Phase Behavior of the Binary and Ternary Mixtures of Biodegradable Poly(E-caprolactone) in Supercritical Fluids" Ind. Eng. Chem. Res. 2006, 45, 3366-33 (Year: 2006).*
Hong, Angela C., et al.; "Perfluorotributylamine: A novel long-lived greenhouse gas"; Geophysical Research Letters, vol. 40, No. 22; Nov. 27, 2013; pp. 6010-6015.
Downs, D.; "Don't Try This At Home: Butane Hash Oil Penalties Stiffen"; East Bay Express; Aug. 11, 2015; 1 page.
Bhattacharjee, Samiran, et al.; "Epoxidation by layered double hydroxide-hosted catalysts. Catalyst synthesis and use in the epoxidation of R-(+)-limonene and (−)-α-pinene using molecular oxygen"; Catalysis letters, vol. 95, No. 3-4; Jun. 2004; pp. 119-125.
Berge, Stephen M., et al.; "Pharmaceutical Salts"; Journal of Pharmaceutical Science, vol. 66, No. 1; Jan. 1977; pp. 1-19.
Croll, Ian M., et al.; "Fluorocarbon Solutions at Low Temperatures. III. Phase Equilibria and Volume Changes in the CH4-CF4 System"; The Journal of Physical Chemistry, vol. 62, No. 8; Aug. 1958; pp. 954-957.
Croll, Ian M., et al.; "Fluorocarbon solutions at low temperatures. IV. The liquid mixtures CH4+CClF3, CH2F2+CClF3, CHF3+CClF3, CF4+CClF3, C2H6+CClF3, C2H6+CF4, and CHF3+CF4"; The Journal of Physical Chemistry, vol. 68, No. 12; Dec. 1964; pp. 3853-3860.
Dantzler, Eleanor M., et al.; "Interaction virial coefficients in fluorocarbon mixtures"; The Journal of Physical Chemistry, vol. 73, No. 5; May 1969; pp. 1335-1341.
Fenby, David V., et al.; "Heats of mixing of nonelectrolyte solutions. IV. Mixtures of fluorinated benzenes"; The Journal of Physical Chemistry, vol. 71, No. 12; Nov. 1967; pp. 4103-4110.
Jolley, J. E., et al.; "Solubility, entropy and partial molal volumes in solutions of gases in non-polar solvents"; Journal of the American Chemical Society, vol. 80, No. 5; Mar. 5, 1958; pp. 1050-1054.
Kielland, Nicola, et al.; "Stereoselective synthesis with carbon dioxide"; Advanced Synthesis & Catalysis, vol. 355, No. 11-12; Aug. 12, 2013; pp. 2115-2138.
Ogura, Haruo, et al.; "A convenient direct synthesis of ureas from carbon dioxide and amines;" Synthesis, vol., No. 05; May 1978; pp. 394-396.
Scott, Robert L.; "The anomalous behavior of fluorocarbon solutions"; The Journal of Physical Chemistry, vol. 62, No. 2; Feb. 1958; pp. 136-145.

(Continued)

*Primary Examiner* — Aaron J Kosar

(74) *Attorney, Agent, or Firm* — Baker & McKenzie LLP

(57) ABSTRACT

Described herein, inter alia, are processes, methods, and compositions useful for the extraction of natural products from source materials.

28 Claims, 2 Drawing Sheets

(56) References Cited

OTHER PUBLICATIONS

Scott, Robert L., et al.; "Solutions of Nonelectrolytes"; Annual Review of Physical Chemistry, vol. 20, No. 1; Oct. 1969; pp. 111-138.

Thorp, N., et al.; "Fluorocarbon Solutions at Low Temperatures. I The Liquid Mixtures CF4-CHF3, CF4-CH4, CF-Kr, CH4-Kr"; The Journal of Physical Chemistry; vol. 60, No. 5; May 1956; pp. 670-673.

Young, Lee W.; International Search Report and Written Opinion for PCT/US2017/065199 dated Mar. 6, 2018; 20 pages.

Noles, Joe R., et al.; "Vapor-Liquid Equilibrium for Chlorodifluoromethane+Dimethyl Ether from 283 to 395 K at Pressure to 5.0 MPa"; J. Chem. Eng. Data (Jul. 1992), 37, pp. 306-310.

Adamczyk, Katrin, Mirabelle Prémont-Schwarz, Dina Pines, Ehud Pines, and Erik TJ Nibbering. "Real-time observation of carbonic acid formation in aqueous solution." Science 326, No. 5960 (Dec. 18, 2009): pp. 1690-1694.

Bernard, Jürgen, Markus Seidl, Ingrid Kohl, Klaus R. Liedl, Erwin Mayer, Óscar Gálvez, Hinrich Grothe, and Thomas Loerting. "Spectroscopic Observation of Matrix-Isolated Carbonic Acid Trapped from the Gas Phase." Angewandte Chemie International Edition 50, No. 8 (Dec. 22, 2010): pp. 1939-1943.

Binks, B. P., P. D. I. Fletcher, S. N. Kotsev, and R. L. Thompson. "Adsorption and aggregation of semifluorinated alkanes in binary and ternary mixtures with hydrocarbon and fluorocarbon solvents." Langmuir 13, No. 25 (Nov. 15, 1997): pp. 6669-6682.

Brady, George W. "Cluster Formation in Perfluoroheptane-iso-Octane Systems near the Consolute Temperature." The Journal of Chemical Physics 32, No. 1 (Jan. 1960): pp. 45-51.

Braga, Mara EM, Rosa MS Santos, Inês J. Seabra, Roselaine Facanali, Márcia OM Marques, and Hermínio C. de Sousa. "Fractioned SFE of antioxidants from maritime pine bark." The Journal of Supercritical Fluids 47, No. 1 (May 29, 2008): pp. 37-48.

Brennecke, Joan F., and Charles A. Eckert. "Phase equilibria for supercritical fluid process design." AIChE Journal 35, No. 9 (Sep. 1989): pp. 1409-1427.

Clare, Bronya, Amal Sirwardana, and Douglas R. MacFarlane. "Synthesis, purification and characterization of ionic liquids." Ionic Liquids, Topics in Current Chemistry, vol. 290; Volume Editor: Barbara Kirchner; Springer Berlin Heidelberg, (May 21, 2009); pp. 1-40.

Coan, C.R., and A.D. King Jr. "Solubility of water in compressed carbon dioxide, nitrous oxide, and ethane. Evidence for hydration of carbon dioxide and nitrous oxide in the gas phase" Journal of the American Chemical Society 93, No. 8 (Apr. 1971): pp. 1857-1862.

Daood, H. G., V. Illés, M. H. Gnayfeed, B. Mészáros, G. Horváth, and P. A. Biacs. "Extraction of pungent spice paprika by supercritical carbon dioxide and subcritical propane." The Journal of Supercritical Fluids 23, No. 2 (Feb. 2002): pp. 143-152.

De Castro, MD Luque, and F. Priego-Capote. "Soxhlet extraction: Past and present panacea." Journal of Chromatography A 1217, No. 16 (Nov. 13, 2009): pp. 2383-2389.

De Melo, M. M. R., A. J. D. Silvestre, and C. M. Silva. "Supercritical fluid extraction of vegetable matrices: applications, trends and future perspectives of a convincing green technology." The Journal of Supercritical Fluids 92 (Aug. 2014): pp. 115-176.

Duce, Celia, Maria Tinè, L. Lepori, E. Matteoli, B. Marongiu, and Alessandra Piras. "A comparative study of thermodynamic properties of binary mixtures containing perfluoroalkanes." Journal of Thermal Analysis and Calorimetry 92, No. 1 (Apr. 2008): pp. 145-154.

Eghbali, Nicolas, and Chao-Jun Li. "Conversion of carbon dioxide and olefins into cyclic carbonates in water." Green Chem. 9, No. 3 (Dec. 21, 2006): pp. 213-215.

Gerig, John T. "Selective solvent interactions in a fluorous reaction system. "Journal of the American Chemical Society 127, No. 25 (Jun. 1, 2005): pp. 9277-9284.

Jha, Sujit Kumar, and Giridhar Madras. "Modeling the solubilities of high molecular weight n-alkanes in supercritical carbon dioxide." Fluid phase equilibria 225 (Nov. 2004): pp. 59-62.

Kan, Huang-Chuan, Ming-Chung Tseng, and Yen-Ho Chu. "Bicyclic imidazolium-based ionic liquids: synthesis and characterization." Tetrahedron 63, No. 7 (Jan. 4, 2007): pp. 1644-1653.

Kihara, Nobuhiro, Nobutaka Hara, and Takeshi Endo. "Catalytic activity of various salts in the reaction of 2, 3-epoxypropyl phenyl ether and carbon dioxide under atmospheric pressure." The Journal of Organic Chemistry 58, No. 23 (Nov. 1993): pp. 6198-6202.

Lagalante, Anthony F., Robert L. Hall, and Thomas J. Bruno. "Kamlet-Taft solvatochromic parameters of the sub-and supercritical fluorinated ethane solvents." The Journal of Physical Chemistry B 102, No. 34 (Jul. 29, 1998): pp. 6601-6604.

Lago, Sara, Héctor Rodríguez, Alberto Arce, and Ana Soto. "Improved concentration of citrus essential oil by solvent extraction with acetate ionic liquids." Fluid Phase Equilibria 361 (Oct. 25, 2013): pp. 37-44.

McLure, I. A., B. Edmonds, and M. Lal. "Extremes in surface tension of fluorocarbon+ hydrocarbon mixtures." Nature Physical Science 241, No. 107 (Jan. 15, 1973): p. 71.

Montañés, Fernando, Tiziana Fornari, Pedro J. Martín-Álvarez, Nieves Corzo, Agustin Olano, and Elena Ibáñez. "Selective recovery of tagatose from mixtures with galactose by direct extraction with supercritical CO2 and different cosolvents." Journal of Agricultural and Food Chemistry 54, No. 21 (Sep. 26, 2006): pp. 8340-8345.

Morgado, Pedro, Jana Black, J. Ben Lewis, Christopher R. Iacovella, Clare McCabe, Luis FG Martins, and Eduardo JM Filipe. "Viscosity of liquid systems involving hydrogenated and fluorinated substances: Liquid mixtures of (hexane+ perfluorohexane)." Fluid Phase Equilibria 358 (Aug. 19, 2013): pp. 161-165.

Poole, Colin F., and Salwa K. Poole. "Extraction of organic compounds with room temperature ionic liquids." Journal of Chromatography A 1217, No. 16 (Sep. 10, 2009): pp. 2268-2286.

Ruckenstein, E., and I. Shulgin. "Aggregation in binary solutions containing hexafluorobenzene." The Journal of Physical Chemistry B 103, No. 46 (Nov. 3, 1999): pp. 10266-10271.

Shiflett, Mark B., Mark A. Harmer, Christopher P. Junk, and A. Yokozeki. "Solubility and diffusivity of 1, 1, 1, 2-tetrafluoroethane in room-temperature ionic liquids." Fluid Phase Equilibria 242, No. 2 (Apr. 2006): pp. 220-232.

Shin, Jungin, Moon Sam Shin, Won Bae, Youn-Woo Lee, and Hwayong Kim. "High-pressure phase behavior of carbon dioxide+ heptadecafluoro-1-decanol system." The Journal of Supercritical Fluids 44, No. 3 (Apr. 2008): pp. 260-265.

Valderrama J. O. and P. A. Robles. "Critical properties, normal boiling temperatures, and acentric factors of fifty ionic liquids." Industrial & Engineering Chemistry Research 46, No. 4 (Jan. 25, 2007): pp. 1338-1344.

Wang, Lijun, and Curtis L. Weller. "Recent advances in extraction of nutraceuticals from plants." Trends in Food Science & Technology 17, No. 6 (Jun. 2006): pp. 300-312.

Williams, Thomas D., Michael Jay, Hans-Joachim Lehmler, Michael E. Clark, Dennis J. Stalker, and Paul M. Bummer. "Solubility enhancement of phenol and phenol derivatives in perfluorooctyl bromide." Journal of pharmaceutical sciences 87, No. 12 (Oct. 14, 1998): pp. 1585-1589.

Zhang, Liang, Jianhua Cheng, Takeshi Ohishi, and Zhaomin Hou. "Copper-Catalyzed Direct Carboxylation of C—H Bonds with Carbon Dioxide." Angew. Chem. Int. Ed. vol. 49, No. 46 (Oct. 4, 2010): pp. 8670-8673.

Hildebrand, Joel H., et al.; Regular Solutions; Jan. 1962; Prentice Hall, Inc.; Englewood Cliffs, NJ.

Downing, Ralph C.; Fluorocarbon Refrigerants Handbook; Jan. 1988; Prentice Hall, Inc.; Englewood Cliffs, NJ.

Tsunashima, Katsuhiko, et al.; "Physical and electrochemical properties of phosphonium ionic liquids derived from trimethylphosphine." Electrochemistry Communications 39 (2014); Dec. 14, 2013; pp. 30-33.

(56) References Cited

OTHER PUBLICATIONS

Rabari, Dharamashi, et al.; "Biobutanol and n-propanol recovery using a low density phosphonium based ionic liquid at T=298.15 K and p=1atm." Fluid Phase Equilibria 355 (2013); Jul. 1, 2013; pp. 26-33.
González, Begoña.; et al.; "Capacity of two 1-butyl-1-methylpyrrolidinium-based ionic liquids for the extraction of ethanol from its mixtures with heptane and hexane." Fluid Phase Equilibria 354; Jun. 19, 2013; pp. 89-94.
Jiao, Jiao; et al.; "Microwave-assisted ionic liquids pretreatment followed by hydro-distillation for the efficient extraction of essential oil from Dryopteris fragrans and evaluation of its antioxidant efficacy in sunflower oil storage." Journal of Food Engineering 117, No. 4; Oct. 27, 3012; pp. 477-485.
Hua, Tian, et al.; "Crystal structure of the human cannabinoid receptor CB 1"; Cell, 167(3); Oct. 20, 2016; 27 pages.
Munro, Sean, et al.; "Molecular characterization of a peripheral receptor for cannabinoids"; Nature, 365(6441); Sep. 2, 1993; pp. 61-65.
Porter, Brenda E., et al.; "Report of a parent survey of cannabidiol-enriched cannabis use in pediatric treatment-resistant epilepsy"; Epilepsy & Behavior 29, No. 3; Dec. 2013; pp. 574-577.
Cooper, Ziva D., et al.; "Comparison of the analgesic effects of dronabinol and smoked marijuana in daily marijuana smokers"; Neuropsychopharmacology 38, No. 10; May 15, 2013; pp. 1984-1992.
Kahan, Meldon, et al.; "Prescribing smoked cannabis for chronic noncancer pain Preliminary recommendations." Canadian Family Physician 60, No. 12; Dec. 2014; pp. 1083-1090.
Wilsey, Barth, et al.; "Low-dose vaporized cannabis significantly improves neuropathic pain." The Journal of Pain 14, No. 2; Feb. 2013; pp. 136-148.
Molina, Patricia E., et al.; "Cannabinoid administration attenuates the progression of simian immunodeficiency virus"; AIDS research and human retroviruses 27, No. 6; Nov. 6, 2011; pp. 585-592.
Svendsen, Kristina B., et al.; "Does the cannabinoid dronabinol reduce central pain in multiple sclerosis? Randomized double blind placebo controlled crossover trial" BMJ 329, No. 7460; Jul. 16, 2004: 8 pages.
Hingorani, Tushar, et al.; "Effect of ion pairing on in vitro transcorneal permeability of a Δ9-tetrahydrocannabinol prodrug: Potential in glaucoma therapy"; Journal of pharmaceutical sciences 101, No. 2; Feb. 2012; pp. 616-626.
Chakravarti, Bandana, et al.; "Cannabinoids as therapeutic agents in cancer: current status and future implications"; Oncotarget 5, No. 15; Jul. 17, 2014; 21 pages.
More, Sandeep Vasant, et al.; "Promising cannabinoid-based therapies for Parkinson's disease: motor symptoms to neuroprotection"; Molecular neurodegeneration 10, No. 1; Apr. 8, 2015; 26 pages.
Fiz, Jimena, et al.; "Cannabis use in patients with fibromyalgia: effect on symptoms relief and health-related quality of life"; PLoS One, vol. 6, No. 4; Apr. 2011; 5 pages.
Perron, Brian E., et al.; "Use of Salvia divinorum in a nationally representative sample"; The American journal of drug and alcohol abuse, vol. 38, No. 1; Aug. 11, 2011; 6 pages.
Potter, David N., et al.; "Repeated exposure to the κ-opioid receptor agonist salvinorin A modulates extracellular signal-regulated kinase and reward sensitivity"; Biological Psychiatry, vol. 70, No. 8; Oct. 15, 2011; pp. 744-753.
Teksin, Zeynep S., et al.; "Evaluation of the transport, in vitro metabolism and pharmacokinetics of Salvinorin A, a potent hallucinogen"; European Journal of Pharmaceutics and Biopharmaceutics, vol. 72, No. 2; Jun. 2009; pp. 471-477.
Riba, Jordi, et al.; "Human pharmacology of ayahuasca: subjective and cardiovascular effects, monoamine metabolite excretion, and pharmacokinetics"; Journal of Pharmacology and Experimental Therapeutics, vol. 306, No. 1; Mar. 26, 2003; pp. 73-83.
Rivier, Laurent, et al.; "Ayahuasca; the South American hallucinogenic drink: An ethnobotanical and chemical investigation"; Economic Botany, vol. 26, No. 2; Apr. 1972; pp. 101-129.

Volz, Hans-Peter, et al.; "Kava-kava extract WS 1490 versus placebo in anxiety disorders: A randomized placebo-controlled 25-week outpatient trial"; Pharmacopsychiatry, vol. 30; Jan. 30, 1997; 5 pages.
Sarris, J., et al.; "The Kava Anxiety Depression Spectrum Study (KADSS): a randomized, placebo-controlled crossover trial using an aqueous extract of Piper methysticum"; Psychopharmacology, vol. 205, No. 3; May 9, 2009; pp. 399-407.
Clouatre, Dallas L. "Kava kava: examining new reports of toxicity"; Toxicology Letters, vol. 150, No. 1; Apr. 15, 2004; pp. 85-96.
Zezula, Josef, et al.; "Recent progress in the synthesis of morphine alkaloids"; Synlett, 2005, No. 3; Feb. 4, 2005; pp. 388-405.
Schiff, Jr., Paul L. "Opium and its alkaloids"; American Journal of Pharmaceutical Education 66.2; Jun. 2002; pp. 188-196.
Tolstikova, T.G., et al.; "Thebaine as a Precursor of Opioid Analgesic Agents"; Chemistry for Sustainable Development, vol. 17; Jan. 2009; pp. 109-126.
Rocha, Fabbla Dutra, et al.; "Potential cytotoxic activity of some Brazilian seaweeds on human melanoma cells"; Phytotherapy Research, vol. 21, No. 2; Feb. 21, 2007; pp. 170-175.
Jha, Rajeev Kumar, et al.; "Biomedical compounds from marine organisms"; Marine Drugs 2.3; Aug. 25, 2004; pp. 123-146.
Thornburg, Christopher C., et al.; "Deep-Sea Hydrothermal Vents: Potential Hot Spots for Natural Products Discovery?"; Journal of Natural Products, vol. 73, No. 3; Jan. 25, 2010; pp. 489-499.
Pettit, George R., et al.; "Antineoplastic agents 315. Isolation and structure of the marine sponge cancer cell growth inhibitor phakellistatin 5"; Bioorganic & Medicinal Chemistry Letters, vol. 4, No. 17; Sep. 8, 1994; pp. 2091-2096.
Yosief, Tesfamariam, et al.; "Asmarines A-F, novel cytotoxic compounds from the marine sponge *Raspailia* species"; Journal of Natural Products, vol. 63, No. 3; Mar. 2000; pp. 299-304.
Numata, Atsushi, et al.; "Gymnastatins, novel cytotoxic metabolites produced by a fungal strain from a sponge"; Tetrahedron Letters, vol. 38, No. 32; Aug. 1997; pp. 5675-5678.
Kobayshi, Jun'ichi, et al.; "Plakotenin, a new cytotoxic carboxylic acid from the okinawan marine sponge *plakortis* Sp."; Tetrahedron Letters, vol. 33, No. 18; Apr. 28, 1992; pp. 2579-2580.
Washida, Kazuto, et al.; "Karatungiols A and B, two novel antimicrobial polyol compounds, from the symbiotic marine dinoflagellate *Amphidinium* sp."; Tetrahedron Letters, vol. 47, No. 15; Feb. 28, 2006; pp. 2521-2525.
Kwon, Hak Cheol, et al.; "Marinomycins A-D, antitumor-antibiotics of a new structure class from a marine actinomycete of the recently discovered genus '*Marinispora*'"; Journal of the American Chemical Society, vol. 128, No. 5; Jan. 13, 2006; pp. 1622-1632.
Yan, Yong-Ming, et al.; "(±)-Aspongamide A, an N-Acetyldopamine Trimer Isolated from the Insect Aspongopus chinensis, Is an Inhibitor of p-Smad3"; Organic Letters, vol. 16, No. 2; Jan. 2, 2014; pp. 532-535.
Whitehouse, M.W., et al.; "Emu oil (s): a source of non-toxic transdermal anti-inflammatory agents in aboriginal medicine"; Inflammopharmacology, vol. 6, No. 1; Mar. 1998; 8 pages.
Nobre, Beatriz P., et al. "Supercritical extraction of lycopene from tomato industrial wastes with ethane"; Molecules, vol. 17, No. 7; Jul. 11, 2012; pp. 8397-8407.
Kendall, Jonathan L., et al.; "Polymerizations in supercritical carbon dioxide"; Chemical Reviews, vol. 99, No. 2; Jan. 22, 1999; pp. 543-563.
Still, W. Clark, et al.; "Rapid chromatographic technique for preparative separations with moderate resolution"; The Journal of Organic Chemistry, vol. 43, No. 14; Jul. 1978; pp. 2923-2925.
Suresh, S.J., et al.; "Hydrogen bond thermodynamic properties of water from dielectric constant data"; The Journal of Chemical Physics, vol. 113, No. 21; Dec. 1, 2000; pp. 9727-9732.
Oster, Gerald, et al.; "The influence of hindered molecular rotation on the dielectric constants of water, alcohols, and other polar liquids"; The Journal of Chemical Physics, vol. 11, No. 4; Apr. 1943; pp. 175-178.

\* cited by examiner

SYSTEMS AND METHODS FOR EXTRACTION OF NATURAL PRODUCTS

CROSS-REFERENCES TO RELATED APPLICATIONS

This application claims the benefit of U.S. Provisional Application No. 62/431,351, filed Dec. 7, 2016, which is incorporated herein by reference in entirety and for all purposes.

BACKGROUND OF THE INVENTION

A major problem in pharmaceutical chemistry relates to extraction of useful substances from plants or animals where such useful substances are employed for the formulation of a pharmaceutical or a nutraceutical. Various processes exist for the extraction of natural products from plant, animal, fungi, bacteria, or virus, but each of these processes suffer from one or more deficiencies. There is an unmet need for a new methodology which can safely and selectively extract desired medicinally or nutritionally valuable components from natural materials.

BRIEF SUMMARY OF THE INVENTION

In a first aspect, is provided a method of extracting a natural organic compound from a natural material, the method including contacting the natural material with an extraction fluid thereby extracting the natural organic compound from the natural material into the extraction fluid to form an extracted fluid solution. The extraction fluid includes a fluorophilic compound and a hydrofluorocarbon.

In another aspect, is provided a fluid including chlorodifluoromethane and dimethylether.

DETAILED DESCRIPTION OF THE INVENTION

I. Definitions

Figure 1:
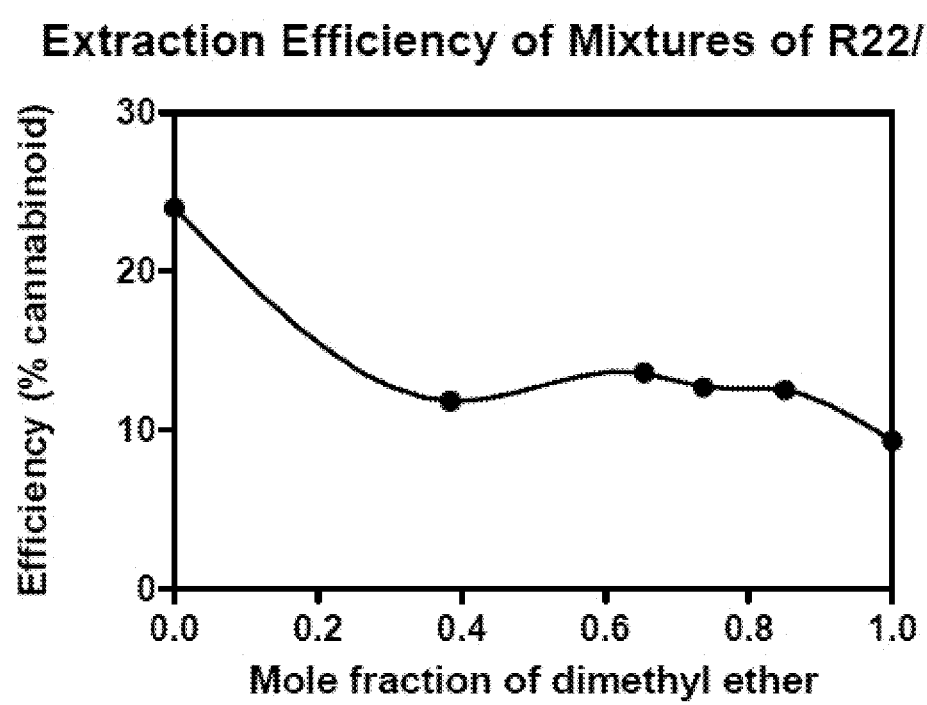
FIG. 1 Graph depicting the efficiency of mixtures of fluorocarbon R22 and dimethyl ether (DME) to extract total cannabinoids in a single 30-minute extraction at 26° C.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$—CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

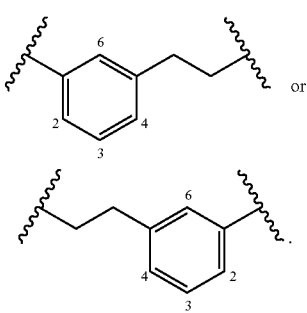

or

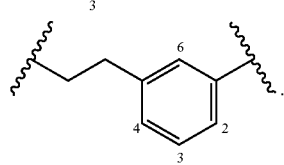

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$ —$SO_3H$, —$OSO_3H$, —$SO_2NH_2$, —$NHNH_2$, —$ONH_2$, —NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cyclalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —$NO_2$, —NR'SO$_2$R", —NR'C(O)R", —NR'C(O)—OR", —NR'OR", in a number ranging from zero to (2 m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')q-U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)r-B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:
(A) oxo, halogen, CF$_3$, CN, OH, NH$_2$, COOH, CONH$_2$, NO$_2$, SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, NHOH, OCF$_3$, OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, heteroaryl, substituted with at least one substituent selected from:
(i) oxo, halogen, CF$_3$, CN, OH, NH$_2$, COOH, CONH$_2$, NO$_2$, SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, NHOH, OCF$_3$, OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(ii) alkyl, heteroalkyl, cycloalkyl, heterocycloalkyl, aryl, heteroaryl, substituted with at least one substituent selected from:
(a) oxo, halogen, CF$_3$, CN, OH, NH$_2$, COOH, CONH$_2$, NO$_2$, SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, NHOH, OCF$_3$, OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, heteroaryl, substituted with at least one substituent selected from: oxo, halogen, CF$_3$, CN, OH, NH$_2$, COOH, CONH$_2$, NO$_2$, SH, —SO$_3$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, NHOH, OCF$_3$, OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkyl ene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of R13A, $R^{13B}$, $R^{13C}$, $R^{13D}$, etc. is defined within the scope of the definition of $R^{13}$ and optionally differently.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

"Selective" or "selectivity" or the like of a compound refers to the compound's ability to discriminate between molecular targets.

"Specific", "specifically", "specificity", or the like of a compound refers to the compound's ability to cause a particular action, such as inhibition, to a particular molecular target with minimal or no action to other proteins in the cell.

"Fungi" are defined as any of a kingdom (Fungi) of saprophytic and parasitic spore-producing eukaryotic typically filamentous organisms formerly classified as plants that lack chlorophyll and include molds, rusts, mildews, smuts, mushrooms, and yeasts. Several other groups that historically have been associated with fungi, such as the slime molds and water molds are now not considered to be fungi. The phyla of fungi are distinguished primarily by their sexual reproductive structures. Yeasts do not form a single taxonomic or phylogenetic grouping. Some yeast such as Candida albicans are human pathogens.

Bacteria constitute a large domain of prokaryotic microorganisms. Bacteria have a number of shapes, ranging from spheres to rods and spirals. Bacterial cells are typically 0.5-5. µm in length. The bacterial cell is surrounded by a cell membrane, which encloses the contents of the cell and acts as a barrier to hold nutrients, proteins and other essential components of the cytoplasm within the cell. In some bacteria, a cell wall is present on the outside of the cell membrane. As they are prokaryotes, bacteria do not usually have membrane-bound organelles in their cytoplasm, and thus contain few large intracellular structures. They lack a true nucleus, mitochondria, chloroplasts and the other organelles present in eukaryotic cells.

A virus is a small infectious agent that replicates only inside the living cells of other organisms. Viruses can infect all types of life forms, from animals and plants to microorganisms, including bacteria and archaea.

The term "animal" is used in accordance with its well understood common meaning and represents a multicellular, eukaryotic organism of the kingdom Animalia (also called Metazoa). Animals are divided into various sub-groups, some of which are: vertebrates (birds, mammals, amphibians, reptiles, fish); molluscs (clams, oysters, octopuses, squid, snails); arthropods (millipedes, centipedes, insects, spiders, scorpions, crabs, lobsters, shrimp); annelids (earthworms, leeches); sponges; and jellyfish.

The term "aromatic compound" refers to an organic compound including at least one aromatic moiety (e.g., aryl or heteroaryl).

As used herein, a "fluorophilic" component is any fluorinated compound such as a linear, branched, cyclic, saturated, or unsaturated fluorinated hydrocarbon. The fluorophilic component can optionally include at least one heteroatom (e.g., O, N, S, P, Si; in the backbone of the component). In some cases, the fluorophilic compound may be highly fluorinated, i.e., at least 30%, at least 50%, at least 70%, or at least 90% of the hydrogen atoms of the component are replaced by fluorine atoms. The fluorophilic component may include a fluorine to hydrogen ratio of, for example, at least 0.2:1, at least 0.5:1, at least 1:1, at least 2:1, at least 5:1, or at least 10:1. In some such embodiments, at least 30%, at least 50%, at least 70%, or at least 90% but less than 100% of the hydrogen atoms of the component are replaced by fluorine atoms. In other cases, the fluorophilic component is perfluorinated, i.e., the component contains fluorine atoms but contains no hydrogen atoms. Fluorophilic components compatible with the present invention may have low toxicity, low surface tension, and the ability to dissolve and transport gases. Examples of types of fluorophilic components include but are not limited to hydrofluorocarbons, chlorofluorocarbons, and perfluorocarbons.

As used herein, a "fluorophilic compound" refers to a class of compounds that includes hydrocarbon and fluorocarbon. In embodiments, fluorophilic compounds does not include the chlorofluorocarbon (e.g. R-11(Trichlorofluoromethane), $CCl_3F$; R-12 (Dichlorodifluoromethane), $CCl_2F_2$; or R-13 (Chlorotrifluoromethane), $CClF_3$). In embodiments, the fluorophilic compound is dimethyl ether, methyl ethyl ether, methyl n-propyl ether, methyl isopropyl ether, methyl-n-butyl ether, diethyl ether, methyl tert-butyl ether, or ethyl tert-butyl ether.

A "fluorocarbon compound" is a compound including fluorine and carbon, but not hydrogen (e.g., no carbon-hydrogen bonds). In embodiments, a fluorocarbon compound is an FC-fluorocarbon compound ("FC"), which consists solely of fluorine and carbon. In embodiments, a fluorocarbon compound is a chlorofluorocarbon (CFC) compound, wherein FC and CFC are common terms used to define refrigerants [see, for example, Downing, Ralph C. Fluorocarbon refrigerants handbook Prentice Hall (1988)]. Examples of fluorocarbon compounds include fluoroether compounds, fluoroketone compounds, fluoroaromatic compounds and fluoroolefin compounds. In embodiments, fluorocarbon compounds also include compounds wherein one or more optional substituents therein may be selected from one or more of bromine, chlorine and iodine. Fluorocarbon molecules may have various structures, including straight or branched chain or cyclic structures. The chemical properties of certain of these compounds, because of the unusual polarity of the carbon-fluorine bond, are unexpected. For example, perfluorotrimethyl iodide, a gas which boils at −22.5° C., is relatively stable in the absence of light (which can produce heterolysis and subsequent free radical formation) even in the presence of water below 100° C. or moderately basic solutions. Brominated perfluorocarbons such as 1-bromo-heptadecaflurooctane ($C_8F_{17}Br$), sometimes designated perfluorooctyl bromide α, ω-dibromo-F-butane; 1-bromopenta-decafluoroheptane ($C_7F_{15}Br$); 1-bromo-nonafluorobutane ($C_4F_9Br$); and 1-bromotridecafluorohexane ($C_6F_{13}Br$) are quite stable under extraction conditions. It is also contemplated that fluorocarbons having nonfluorinated substituents, such as perfluorooctyl chloride, or perfluorooctyl hydride may be used in the apparatus, methods, and compositions described herein, as well as similar compounds having different numbers of carbon atoms, e.g., 2-8 carbon atoms. Those skilled in the art will appreciate that esters, thioesters, amines, amides, and other variously modified fluorocarbon-hydrocarbon compounds are also encompassed within the definition of fluorocarbon materials suitable for use in the present invention. Certain perfluorinated compounds are relatively inert and have unexpected properties; for example perfluorotributylamine is not at all basic. See, for example, Hong, Angela C., Cora J. Young, Michael D. Hurley, Timothy J. Wallington, and Scott A. Mabury. "Perfluorotributylamine: A novel long-lived greenhouse gas." Geophysical Research Letters 40, no. 22 (2013): 6010-6015, which is incorporated herein by reference for all purposes.

A "hydrofluorocarbon compound" is a compound including fluorine, carbon and at least one hydrogen atom (e.g., at least one carbon-hydrogen bond). In embodiments, a hydrofluorocarbon compound is an HFC-hydrofluorocarbon compound ("HFC"), which consists solely of fluorine, carbon and hydrogen. In embodiments, a hydrofluorocarbon compound is a hydrochlorofluorocarbon (HCFC) compound. HFC and HCFC are common terms used to define refrigerants (see Downing, Ralph C. supra.). Non-limiting examples of hydrofluorocarbons include trifluoromethane (HFC-23), difluoromethane (HFC-32), pentafluoroethane (HFC-125), 1,1,2,2-tetrafluoroethane (HFC-134), 1,1,1,2-tetrafluoroethane (HFC-134a), 1,1,1-trifluoroethane (HFC-143a), 1,1-difluoroethane (HFC-152a) and fluoroethane (HFC-161). Hydrofluorocarbon compounds may be hydrofluoroether compounds, hydrofluoroketone compounds, hydrofluoroaromatic compounds or hydrofluoroolefin compounds. Non-limiting examples of hydrofluorocarbon compounds include methyl nonafluoroisobutyl ether, methyl nonafluorobutyl ether, ethyl nonafluoroisobutyl ether, ethyl nonafluorobutyl ether, and 3-ethoxy-1,1,1,2,3,4,4,5,5,6,6,6-dodecafluoro-2-trifluoromethylhexane. In embodiments, hydrofluorocarbon compounds include compounds wherein one or more optional substituents may be one or more bromine, chlorine, or iodine. In embodiments, the hydroflurocarbon is chlorodifluoromethane, methyl nonafluoroisobutyl ether, methyl nonafluorobutyl ether, ethyl nonafluoroisobutyl ether, ethyl nonafluorobutyl ether, 3-ethoxy-1,1,1,2,3,4,4,5,5,6,6,6-dodecafluoro-2-trifluoromethylhexane.trifluoromethane (HFC-23), difluoromethane (HFC-32), pentafluoroethane (HFC-125), 1,1,2,2-tetrafluoroethane (HFC-134), 1,1,1,2-tetrafluoroethane (HFC-134a), 1,1,1-trifluoroethane (HFC-143a), 1,1-difluoroethane (HFC-152a), (1,1,1,3,3,3-hexafluoro-2-(fluoromethoxy)propane, 1,2,2,2-tetrafluoroethyl difluoromethyl ether, 2-chloro-1,1,2,-trifluoroethyl difluoromethyl ether, 1-chloro-2,2,2-trifluoroethyl difluoromethyl ether, 2,2-dichloro-1,1-difluoromethyl ether, or fluoroethane (HFC-161).

Within the class of fluorophilic compounds, hydrofluorocarbon compounds, and fluorocarbon compounds, "optionally substituted" indicates that one or more fluorine or hydrogen atoms may be replaced with an independently selected alkane, alkene, alkoxy, fluoroalkoxy, perfluoroalkoxy, fluoroalkyl, perfluoroalkyl, aryl or heteroaryl group or compound (e.g., one or more hydrogens on the carbon chain of the group or compound may be independently substituted with one or more of independently selected substitutents (e.g., substituent groups). For example, a substituted $C_2H_5$ group may, without limitation, be $—CF_2CF_3$, $—CH_2CH_2OH$ or $—CF_2CF_2I$.

A "refrigerant" is a substance that is capable of removing heat from its surroundings (e.g., when it changes phase from liquid to vapor (i.e. when it evaporates)). Refrigerants may add heat to its surroundings in a complementary reaction (e.g., when it changes phase from vapor to liquid (i.e. when it condenses)) (e.g., FC-fluorocarbon, an HFC-hydrofluorocarbon, a chlorofluorocarbon, a hydrochlorofluorocarbon, an alkane, an alkene, or an aromatic compound; or ammonia, carbon dioxide or other gases such as hydrogen, oxygen, nitrogen and argon). Refrigerant substances may contain oxygen, or bromine, chlorine or iodine, as described above, for example, in relation to hydrofluorocarbon and fluorocarbon compounds.

An "azeotrope", or an "azeotropic" or "constant boiling" is a mixture of two or more components whose proportions cannot be altered by simple distillation. When boiled, the vapor has the same proportions of the constituents as the un-boiled mixture. In embodiments, a constant boiling mixture is a "near-azeotropic" mixture, which is a mixture that maintains a substantially constant vapor pressure even after evaporative losses, thereby exhibiting constant boiling behavior. Azeotropic and constant boiling mixtures also include mixtures wherein the boiling points of two or more of the components thereof are separated by only about 5° C. or less.

The "critical pressure" of a substance is the pressure required to liquefy a gas at its critical temperature, which is the temperature at and above which vapor of the substance cannot be liquefied, regardless of how much pressure is applied.

As used herein, "nonaqueous" is meant to define material such as a fluid that is immiscible with water. That is, a liquid that when mixed with water will form a stable two-phase mixture. The non-aqueous phase need not be liquid, but can be a solid or semi-solid lipid or other nonpolar substance that is not soluble in water. In some instances, the nonaqueous phase can include a lipophilic component (e.g., a hydrocarbon) or a fluorinated component (e.g., a fluorocarbon). The aqueous phase can be any liquid miscible with water; that is, any liquid that, when admixed with water, can form a room-temperature, single-phase solution that is stable. In some cases, the aqueous phase can comprise one or more physiologically acceptable reagents and/or solvents, etc.

Non-limiting examples of aqueous phase materials include (besides water itself) methanol, ethanol, DMF (dimethylformamide), or DMSO (dimethyl sulfoxide).

The term "chirality" refers to the geometric property of a rigid object (or spatial arrangement of points or atoms) of being non-superimposable on its mirror image. If the object is superimposable on its mirror image the object is described as being achiral.

The term "chiral center" refers to an atom holding a set of ligands in a spatial arrangement, which is not superimposable on its mirror image. A chirality center may be considered a generalized extension of the concept of the asymmetric carbon atom to central atoms of any element. Each chiral center (*C) is labeled R or S according to a system by which its substituents are each designated a priority according to the Cahn Ingold Prelog priority rules (CIP), based on atomic number.

The term, "enantiomer" refers to one of a pair of optical isomers containing one or more asymmetric carbons whose molecular configurations have left- and right-hand (chiral) forms. Enantiomers have identical physical properties, except for the direction of rotation of the plane of polarized light. Enantiomers have identical chemical properties except toward optically active reagents.

An "ionic liquid" is a salt in liquid form. In embodiments, an ionic liquid includes an organic compound (e.g., and counter ion), typically a salt of an organic acid and an organic base, which may exist in a zwitterionic form, which is present in a liquid state (e.g., at room temperature or substantially close to room temperature, wherein room temperature is defined as a range of temperatures from about 4° C. to about 50° C., and most typically between 15° C. and 30° C., and more typically about 25° C.). In embodiments, an ionic liquid differs from most salts in that it has a very low melting point, and tends to be liquid over a wide temperature range. In embodiments, an ionic liquid is not soluble in non-polar hydrocarbons; is immiscible with water, depending on the anion; or is highly ionizing (but has a low dielectric strength). In embodiments, an ionic liquid has essentially no vapor pressure, most are air and water stable, and they can either be neutral, acidic or basic. In embodiments, the properties of an ionic liquid can be tailored by varying the cation and anion. In embodiments, the cation or anion of an ionic liquid can be any cation or anion such that the cation and anion together form an organic salt that is liquid at or below about 100° C. In embodiments, an ionic liquid is formed by reacting a nitrogen-containing heterocyclic ring, preferably a heteroaromatic ring, with an alkylating agent (for example, an alkyl halide) to form a quaternary ammonium salt, and performing ion exchange or other suitable reactions with various Lewis acids or their conjugate bases to form the ionic liquid. Examples of suitable heteroaromatic rings include substituted pyridines, imidazole, substituted imidazole, pyrrole and substituted pyrroles. In embodiments, these rings can be alkylated with virtually any straight, branched or cyclic $C_1$-$C_{20}$ alkyl group (e.g., the alkyl groups are $C_1$-$C_{16}$ groups). In embodiments, various triarylphosphines, thioethers and cyclic and non-cyclic quaternary ammonium salts may also be used for this purpose. In embodiments, counterions that may be used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoalurninate, perchlorate, hydroxide anion, copper dichloride anion, iron trichloride anion, zinc trichloride anion, as well as various lanthanum, potassium, lithium, nickel, cobalt, manganese, or other metal-containing anions. In embodiments, ionic liquids may be synthesized by salt metathesis, by an acid-base neutralization reaction or by quaternizing a selected nitrogen-containing compound; or they may be obtained commercially from several companies such as Merck (Darmstadt, Germany) or BASF (Mount Olive, N.J.). Representative examples of useful ionic liquids are described in sources such as Clare, Bronya, Amal Sirwardana, and Douglas R. MacFarlane. "Synthesis, purification and characterization of ionic liquids." In Ionic Liquids, pp. 1-40. Springer Berlin Heidelberg, 2010; Valderrama, J. O., and P. A. Robles. "Critical properties, normal boiling temperatures, and acentric factors of fifty ionic liquids." Industrial & Engineering Chemistry Research 46, no. 4 (2007): 1338-1344; Kan, Huang-Chuan, Ming-Chung Tseng, and Yen-Ho Chu. "Bicyclic imidazolium-based ionic liquids: synthesis and characterization." Tetrahedron 63, no. 7 (2007): 1644-1653; Tsunashima, Katsuhiko, Yuki Sakai, and Masahiko Matsumiya. "Physical and electrochemical properties of phosphonium ionic liquids derived from trimethylphosphine." Electrochemistry Communications 39 (2014): 30-33; Poole, Colin F., and Salwa K. Poole. "Extraction of organic compounds with room temperature ionic liquids." Journal of Chromatography A 1217, no. 16 (2010): 2268-2286; Rabari, Dharamashi, and Tamal Banerjee. "Biobutanol and n-propanol recovery using a low density phosphonium based ionic liquid at T=298.15 K and p=1atm." Fluid Phase Equilibria 355 (2013): 26-33; Gonzalez, Begoña, and Sandra Corderi. "Capacity of two 1-butyl-1-methylpyrrolidinium-based ionic liquids for the extraction of ethanol from its mixtures with heptane and hexane." Fluid Phase Equilibria 354 (2013): 89-94; Lago, Sara, Hector Rodriguez, Alberto Arce, and Ana Soto. "Improved concentration of citrus essential oil by solvent extraction with acetate ionic liquids." Fluid Phase Equilibria 361 (2014): 37-44; see also Jiao, Jiao, Qing-Yan Gai, Yu-Jie Fu, Yuan-Gang Zu, Meng Luo, Wei Wang, and Chun-Jian Zhao. "Microwave-assisted ionic liquids pretreatment followed by hydro-distillation for the efficient extraction of essential oil from Dryopteris fragrans and evaluation of its antioxidant efficacy in sunflower oil storage." Journal of Food Engineering 117, no. 4 (2013): 477-485; Shiflett, Mark B., Mark A. Harmer, Christopher P. Junk, and A. Yokozeki. "Solubility and diffusivity of 1,1,1,2-tetrafluoroethane in room-temperature ionic liquids." Fluid phase equilibria 242, no. 2 (2006): 220-232, which are incorporated herein by reference for all purposes. A library, i.e. a combinatorial library, of ionic liquids may be prepared, for example, by preparing various alkyl derivatives of the quaternary ammonium cation, and varying the associated anions. The acidity of the ionic liquids can be adjusted by varying the molar equivalents and type and combinations of Lewis acids.

The term "non-ideal mixture" or "non-ideal fluid" refers to a fluid mixture wherein the enthalpy of mixing is non-zero and the volume change upon mixing is non-zero. In embodiments, a non-ideal mixture displays a vapor pressure lower than expected from Raoult's law (negative deviation), which may be evidence of adhesive forces between different components of the mixture being stronger than the average cohesive forces between the like components. When cohesive forces between like components are stronger than between different components, the vapor pressure is greater than expected from Raoult's law (positive deviation).

The term "supercritical fluid" refers to any substance at a temperature and pressure above its critical point, where distinct liquid and gas phases do not exist. It can effuse through solids like a gas, and dissolve materials like a liquid.

The term "essential oil" refers to a concentrated liquid (e.g., hydrophobic) containing volatile aroma compounds from plants. Essential oils may also be called volatile oils, ethereal oils, aetherolea, or simply as the oil of the plant from which they were extracted, such as oil of clove. An oil is "essential" in the sense that it contains the "essence of" the plant's fragrance—the characteristic fragrance of the plant from which it is derived.

The term "natural" as used for "natural product" and "natural organic compound" refers to something that is found in, or isolated from, nature and is not itself synthetic, artificial, and/or man-made. In some embodiments, a "natural product" is a molecule, compound, or substance that is produced by a living organism, i.e., is found in nature. In some embodiments, natural products are isolated from natural sources that are produced by pathways of primary and secondary metabolism. In some embodiments, natural products are isolated from natural sources that are produced where expression of the product is influenced artificially. In some embodiments, natural products are isolated from natural sources that are produced through over-expression of the natural product. In some embodiments, a "natural organic compound" is a purified organic (carbon-containing chemical) compound isolated from natural sources. In some embodiments, a natural organic compound is isolated from natural sources including plant, animal, fungus, virus, and bacteria. In some embodiments, natural organic compounds are isolated from natural sources that have been genetically modified or engineered, including plant, animal, fungus, virus, and bacteria. In some embodiments, natural organic compounds are isolated from natural sources through extraction. In some embodiments, natural organic compounds are isolated from natural sources through extraction methods as described herein.

The term "flavonoid" (or bioflavonoid) refers to a class of plant and fungus secondary metabolites. Flavonoids have the general structure of a 15-carbon skeleton, which consists of two phenyl rings and a heterocyclic ring. In some embodiments, flavonoids are classified as flavonoids (or bioflavonoids), isoflavonoids (derived from 3-phenylchromen-4-one (3-phenyl-1,4-benzopyrone) structure), and neoflavonoids (derived from 4-phenylcoumarine (4-phenyl-1,2-benzopyrone) structure). The term "prenylflavonoid" (or prenylated flavonoids) refers to a subclass of flavonoids. Chemically, they have a prenyl group attached to the flavonoid backbone.

The term "kavalactone" refers to a class of lactone compounds found in the kava plant. In some embodiments, kavalactones possess a wide variety of pharmacological effects including analgesic, anticonvulsant, amnestic, nootropic, and sedative activity.

The term "salvorin" refers to a terpenoid with psychotropic properties found in the *Salvia divinorum* plant.

The term "terpene" refers to a large class of hydrocarbon organic compound found in a variety of plants, including conifers, and some insects, such as termites and swallowtail butterflies. Terpenes are derived biosynthetically from units of isoprene, which has the molecular formula $C_5H_8$. The basic molecular formulae of terpenes are multiples of that, $(C_5H_8)_n$ where n is the number of linked isoprene units. This is called the isoprene rule or the C5 rule. In some embodiments, terpenes are the primary constituents of the essential oils of many flowers and plants. Terpenes may include monoterpenes, diterpenes, sesquiterpenes, triterpenes, sesterterpenes, norterpenes, nortriterpenes, and norsesquiterpenes. Diterpenes refers to diterpene acids, esters, alkaloids (such as indolo-terpenes) which are composed of two isoprene units.

In embodiments, the terpene is a camphor or a derivative, analog, or prodrug thereof (e.g., 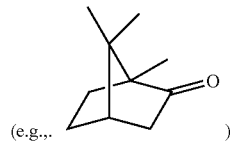 )

In embodiments, the terpene is a carvone or a derivative, analog, or prodrug thereof (e.g., 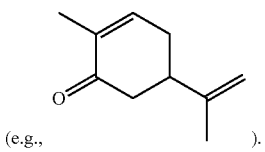 ).

In embodiments, the terpene is a limonene or a derivative, analog, or prodrug thereof (e.g., 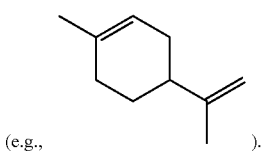 ).

In embodiments, the terpene is a linalool or a derivative, analog, or prodrug thereof (e.g., 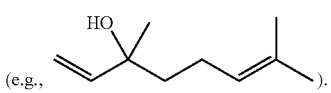 ).

In embodiments, the terpene is a geraniol or a derivative, analog, or prodrug thereof (e.g. 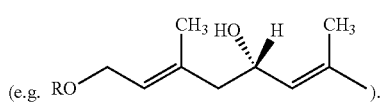 ).

In embodiments, the terpene is a pinene or a derivative, analog, or prodrug thereof (e.g. 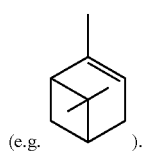 ).

In embodiments, the terpene is a ionone or a derivative, analog, or prodrug thereof (e.g., 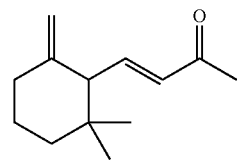 ).

In embodiments, the terpene is a iridoid or a derivative, analog, or prodrug thereof (e.g.,

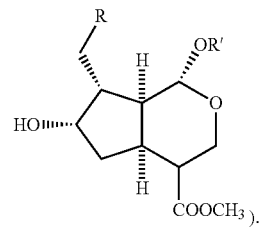 ).

In embodiments, the terpene is a abietane or a derivative, analog, or prodrug thereof (e.g., 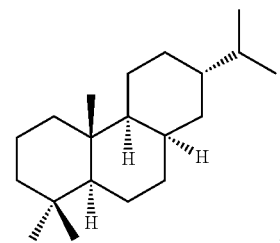 ).

In embodiments, the terpene is a atisane or a derivative, analog, or prodrug thereof (e.g., 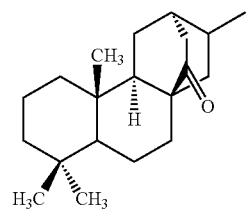 ).

In embodiments, the terpene is a basmane or a derivative, analog, or prodrug thereof (e.g., 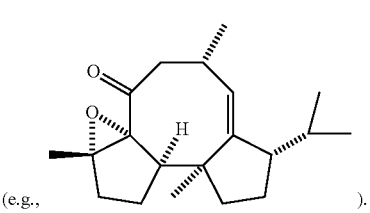 ).

In embodiments, the terpene is a briarane or a derivative, analog, or prodrug thereof (e.g., 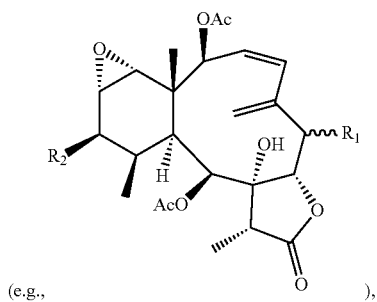), wherein Ac refers to an acetyl group; ∿∿∿ refers to a bond designating a mix of stereoisomers; $R_1$ refers to a moiety selected from —Cl and —OAc (acetic acid) and $R_2$ is a moiety selected from —OH, —OAc, —OCOCH$_2$CH(CH$_3$)$_2$, —OCOCH$_3$, —OCOCH$_2$CH$_3$ (propionate).

In embodiments, the terpene is a carophyllene or a derivative, analog, or prodrug thereof (e.g., 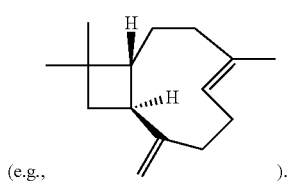).

In embodiments, the terpene is a casbane or a derivative, analog, or prodrug thereof (e.g. 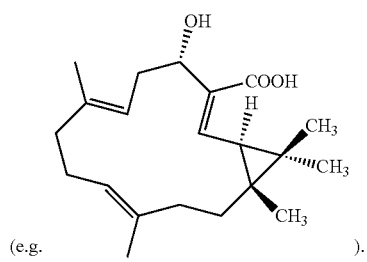).

In embodiments, the terpene is a cassane or a derivative, analog, or prodrug thereof (e.g. 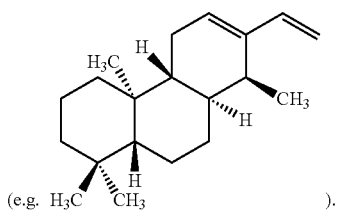).

In embodiments, the terpene is a cembranoid or a derivative, analog, or prodrug thereof (e.g., 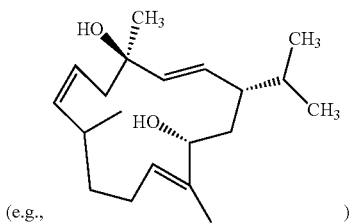 [SMILES: C/C1=C\CCC(C)/C=C\C[C@@](C)(O)/C=C/[C@H](C(C)C)C[C@H]1O])

In embodiments, the terpene is a norcembranoid or a derivative, analog, or prodrug thereof (e.g. 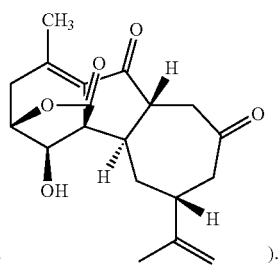).

In embodiments, the terpene is a bicembrane or a derivative, analog, or prodrug thereof (e.g. 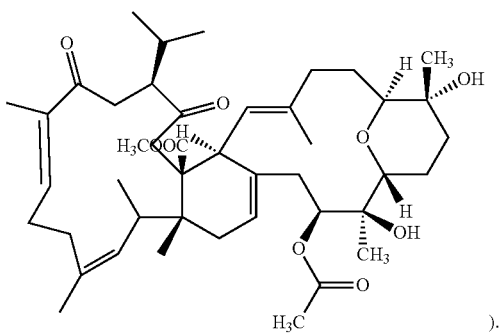).

In embodiments, the terpene is a cladiellane or a derivative, analog, or prodrug thereof (eg. 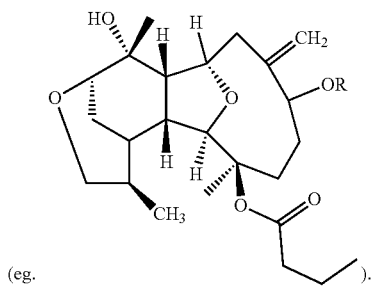).

In embodiments, the terpene is a clerodane or a derivative, analog, or prodrug thereof

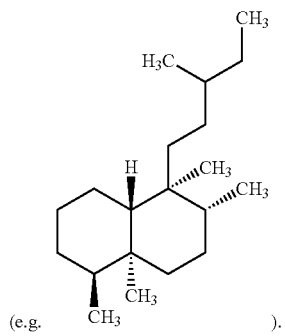 [SMILES: CCC(C)CC[C@]1(C)[C@H]2CCC[C@H](C)[C@]2(C)CC[C@H]1C]

(e.g. ).

In embodiments, the terpene is a curcusone or a derivative, analog, or prodrug thereof

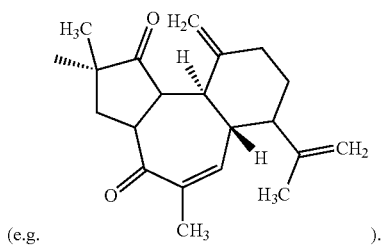

(e.g. ).

In embodiments, the terpene is a cyathane or a derivative, analog, or prodrug thereof

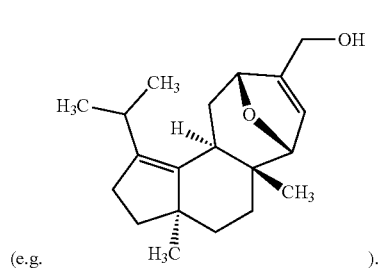 [SMILES: CC(C)C1=C2[C@H]3C[C@H]4O[C@H](C=C4CO)[C@]3(C)CC[C@@]2(C)CC1]

(e.g. ).

In embodiments, the terpene is a daphnane or a derivative, analog, or prodrug thereof

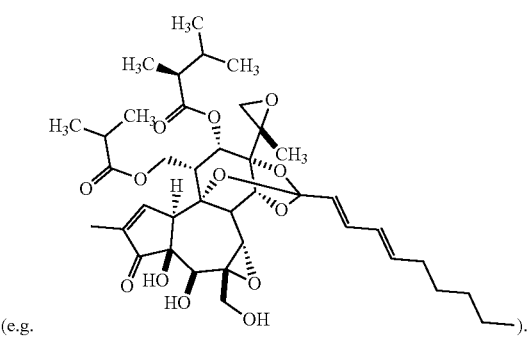 [SMILES: CCCCC/C=C/C=C/C12O[C@@H]3C4[C@@H]5O[C@]5(CO)[C@@H](O)[C@]5(O)C(=O)C(C)=C[C@H]5[C@@]4(O1)[C@H](COC(=O)C(C)C)[C@H](OC(=O)[C@@H](C)C(C)C)[C@]3([C@]1(C)CO1)O2]

(e.g. ).

In embodiments, the terpene is a dolabellane or a derivative, analog, or prodrug thereof

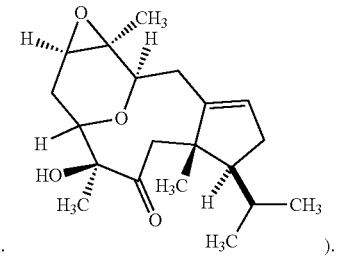

(e.g. ).

In embodiments, the terpene is a drimane or a derivative, analog, or prodrug thereof

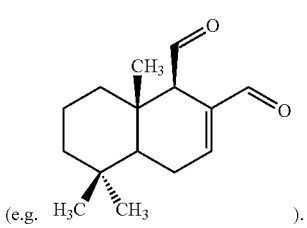

(e.g. ).

In embodiments, the terpene is a pimane or a derivative, analog, or prodrug thereof

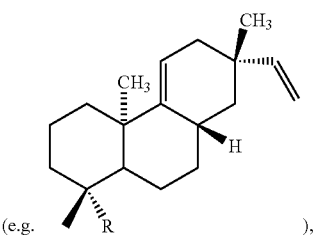

(e.g. ), wherein R is a moiety selected from —H, —OH, —CH$_2$OH, —CO$_2$CH$_3$, —CHO, —CH$_2$OAc, —COOH, and —CH$_3$.

In embodiments, the terpene is a ent-pimane or a derivative, analog, or prodrug thereof

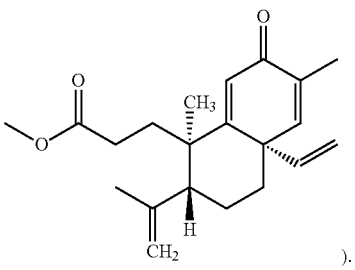

(e.g. ).

In embodiments, the terpene is a eudesmane or a derivative, analog, or prodrug thereof (e.g. 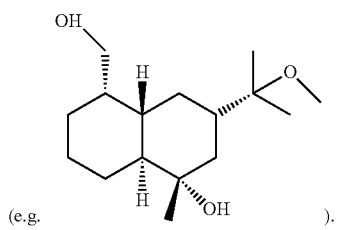 ).

In embodiments, the terpene is a eunicellin or a derivative, analog, or prodrug thereof (e.g. 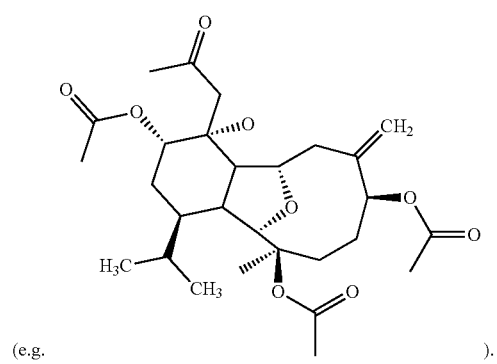 [SMILES: C=C1C[C@@H]2O[C@@H](C3C2[C@](O)(CC(C)=O)[C@@H](OC(C)=O)C[C@@H]3C(C)C)[C@](C)(OC(C)=O)CC[C@@H]1OC(C)=O] ).

In embodiments, the terpene is a franchetine or a derivative, analog, or prodrug thereof (e.g. 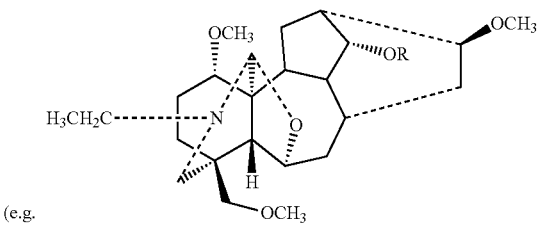 ), wherein R represents a benzyl group.

In embodiments, the terpene is a gibberelin or a derivative, analog, or prodrug thereof (e.g. 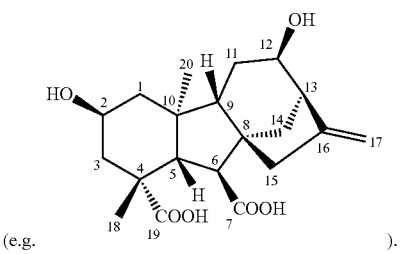 [SMILES: C=C1C[C@]23C[C@H]1[C@H](O)C[C@H]2[C@]1(C)C[C@H](O)C[C@@](C)(C(=O)O)[C@H]1[C@@H]3C(=O)O] ).

In embodiments, the terpene is a grayane or a derivative, analog, or prodrug thereof (e.g., 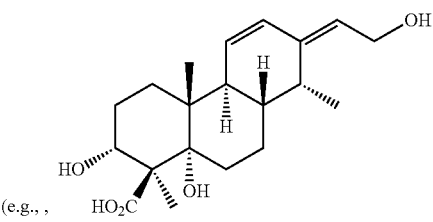 ).

In embodiments, the terpene is a guaiene or a derivative, analog, or prodrug thereof (e.g., 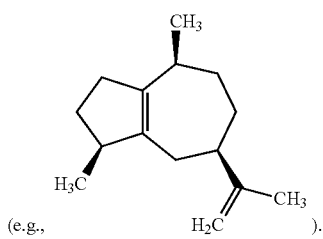 ).

In embodiments, the terpene is a Guanacastane or a derivative, analog, or prodrug thereof (e.g., 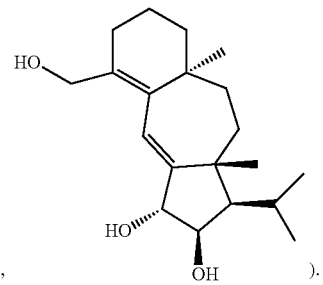 ).

In embodiments, the terpene is a icetaxane or a derivative, analog, or prodrug thereof (e.g., 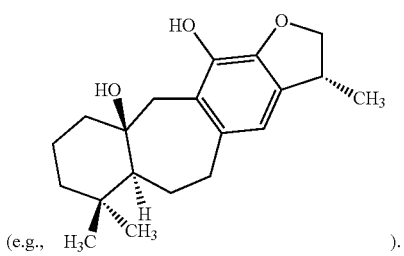 ).

In embodiments, the terpene is a isofregenedane or a derivative, analog, or prodrug thereof (e.g., 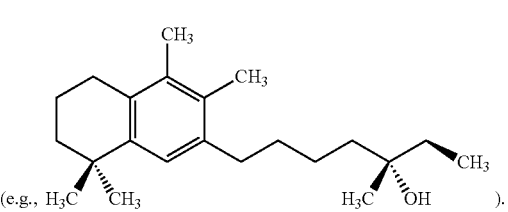 ).

In embodiments, the terpene is a jatrophane or a derivative, analog, or prodrug thereof

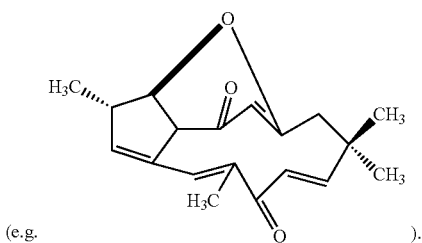

(e.g. ).

In embodiments, the terpene is a kalihinene or a derivative, analog, or prodrug thereof

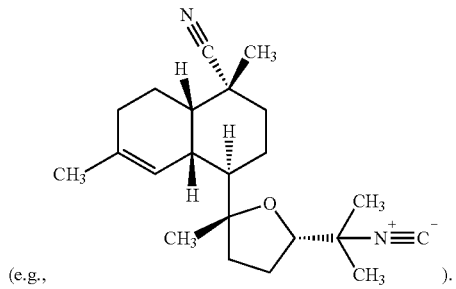

(e.g., ).

In embodiments, the terpene is a kaurane or a derivative, analog, or prodrug thereof

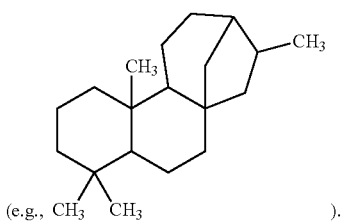

(e.g., ).

In embodiments, the terpene is a kempane or a derivative, analog, or prodrug thereof

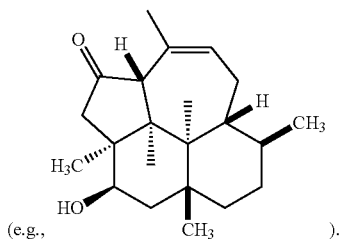

(e.g., ).

In embodiments, the terpene is a labdane or a derivative, analog, or prodrug thereof

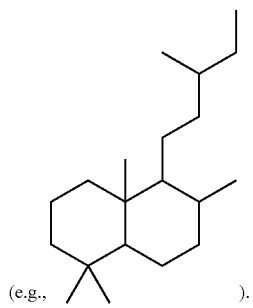

(e.g., ).

In embodiments, the terpene is a grindelane labdane or a derivative, analog, or prodrug thereof

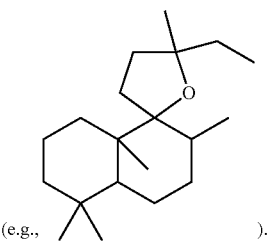

(e.g., ).

In embodiments, the terpene is a lathyrane or a derivative, analog, or prodrug thereof

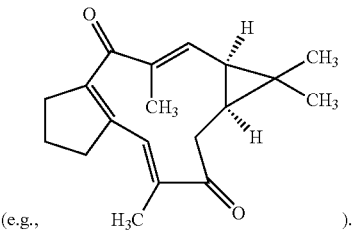 [SMILES: C/C1=C\C2=C(CCC2)C(=O)/C(C)=C/[C@@H]2[C@H](CC1=O)C2(C)C]

(e.g., ).

In embodiments, the terpene is a laurenene or a derivative, analog, or prodrug thereof

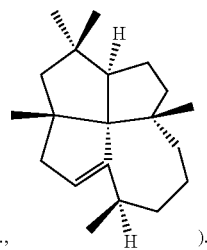

(e.g., ).

In embodiments, the terpene is a lobane (e.g., lobatriene) or a derivative, analog, or prodrug thereof

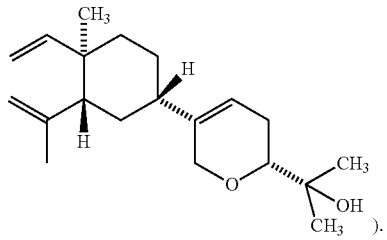

(e.g., ).

In embodiments, the terpene is a mulinane or a derivative, analog, or prodrug thereof

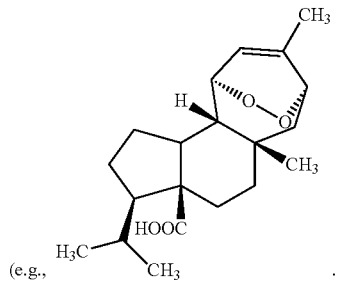 [SMILES: CC1=C[C@H]2OO[C@@H]1C[C@]1(C)CC[C@@]3(C(=O)O)C(CC[C@@H]3C(C)C)[C@H]21]

(e.g., ).

In embodiments, the terpene is a myrsinol or a derivative, analog, or prodrug thereof (e.g., 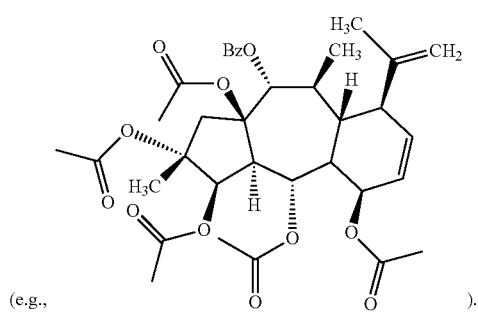).

In embodiments, the terpene is a pepluane or a derivative, analog, or prodrug thereof (e.g., 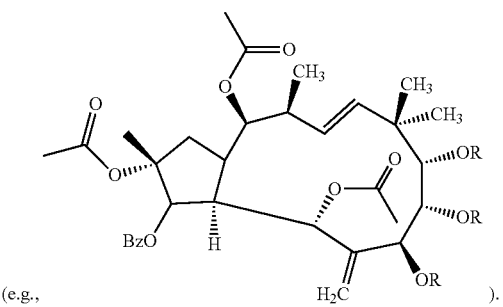).

In embodiments, the terpene is a phorbol or a derivative, analog, or prodrug thereof (e.g., phorbol 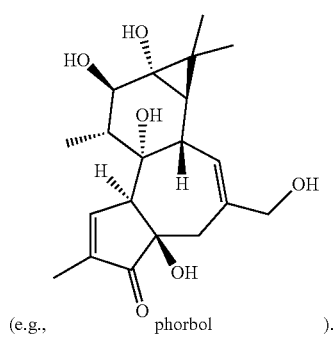).

In embodiments, the terpene is a rosane or a derivative, analog, or prodrug thereof (e.g., 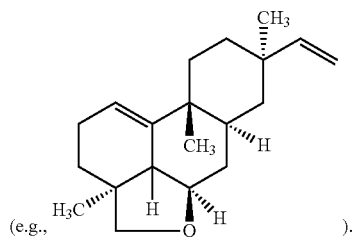).

In embodiments, the terpene is a sclaerol or a derivative, analog, or prodrug thereof (e.g., 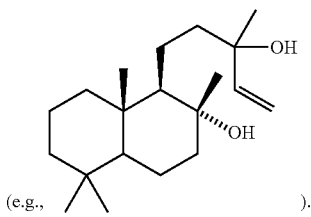 [SMILES: C=CC(C)(O)CC[C@@H]1[C@@]2(C)CCCC(C)(C)C2CC[C@@]1(C)O]).

In embodiments, the terpene is a scopadulane or a derivative, analog, or prodrug thereof (e.g., 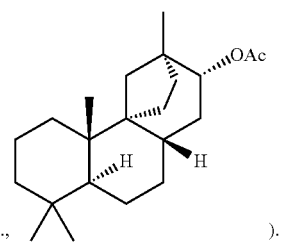).

In embodiments, the terpene is a serrulatane or a derivative, analog, or prodrug thereof (e.g., 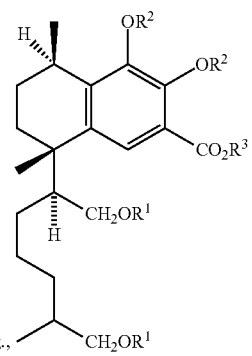), wherein $R_1$ is a moiety selected from —H, —OH, —N, —NH, —NOH, —CH$_3$, —CO-heteroaryl, —CH$_2$OCOC$_4$H$_3$N$_2$, —CNOH, —CH$_2$, and

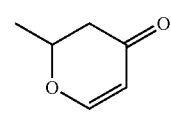

and $R_2$ is a moiety selected from —H, —NO$_2$, —CH$_3$, and halogen.

In embodiments, the terpene is a spatane or a derivative, analog, or prodrug thereof (e.g., 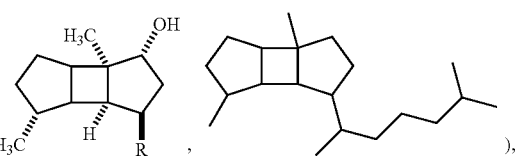), wherein R is a moiety selected from —H, —OH, —CH$_2$CH$_3$ (CH$_2$)$_4$(CH$_3$)$_2$, and —CH$_3$.

In embodiments, the terpene is a stemodane or a derivative, analog, or prodrug thereof

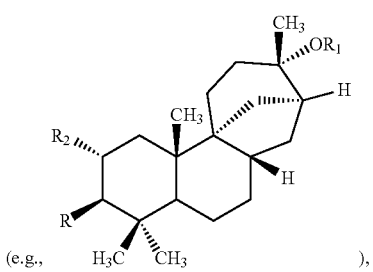

(e.g., ), wherein R is a moiety selected from —H, —OH, —CH$_3$, and —OCH$_3$; R$_1$ is a moiety selected from —H, —OH, —CH$_2$OH, and —CH$_3$; and R$_2$ is a moiety selected from —H, —OH, and —O.

In embodiments, the terpene is a taxane or a derivative, analog, or prodrug thereof (e.g.,

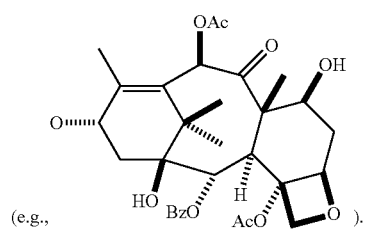

).

In embodiments, the terpene is a tigliane or a derivative, analog, or prodrug thereof

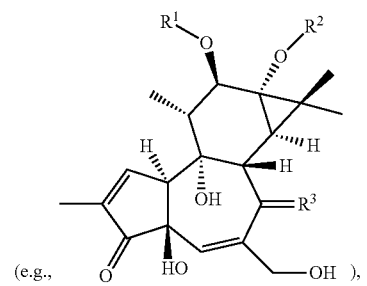

(e.g., ), wherein R$_1$ is a moiety selected from —H, —CH$_3$, —COC$_{11}$H$_{23}$, —CH$_2$OH, —Bz, —OAc, 2-methylbutryrl, and

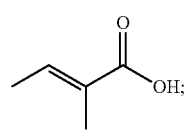

R$_2$ is a moiety selected from —CH3, —COCH3, —Bz, —OAc, isobutryryl, and 2-methylbutryrl; and R$_3$ is a moiety selected from —O, and —CH$_2$.

In embodiments, the terpene is a tormesane (e.g., tormesolane) or a derivative, analog, or prodrug thereof

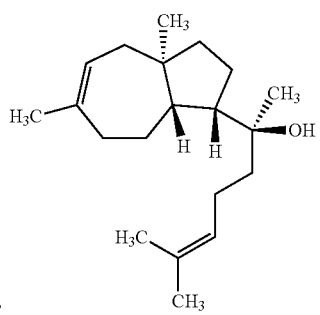

(e.g., ).

In embodiments, the terpene is a valparane or a derivative, analog, or prodrug thereof

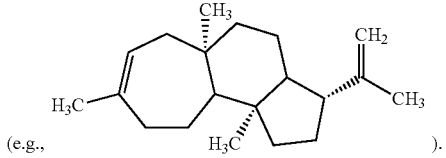

(e.g., ).

In embodiments, the terpene is a vibsane or a derivative, analog, or prodrug thereof

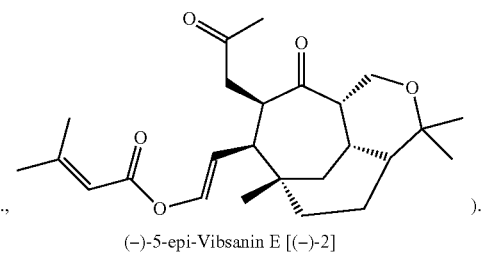

(e.g., ).

(−)-5-epi-Vibsanin E [(−)-2]

In embodiments, the terpene is a xenicane or a derivative, analog, or prodrug thereof

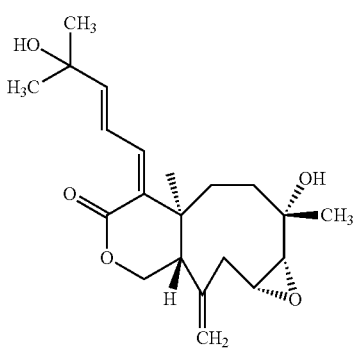

(e.g., ).

In embodiments, the terpene is a bakkane or a derivative, analog, or prodrug thereof

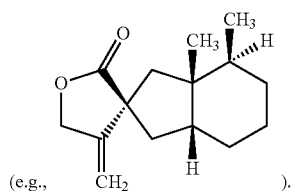 [SMILES: C=C1COC(=O)[C@@]12C[C@H]1CCC[C@H](C)[C@@]1(C)C2]

In embodiments, the terpene is a bisabolane or a derivative, analog, or prodrug thereof

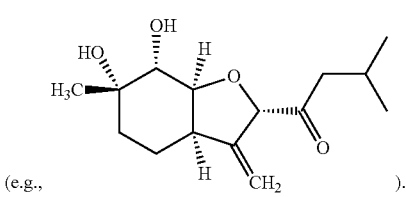 [SMILES: C=C1[C@@H](C(=O)CC(C)C)O[C@H]2[C@@H]1CC[C@](C)(O)[C@@H]2O]

In embodiments, the terpene is a zizanoic acid or a derivative, analog, or prodrug thereof

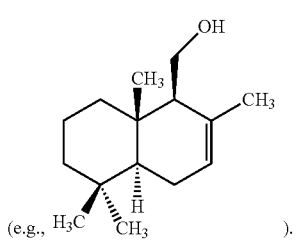

In embodiments, the terpene is a drimenol or a derivative, analog, or prodrug thereof

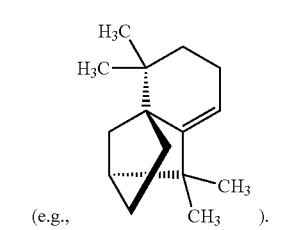

In embodiments, the terpene is a isolongifolene or a derivative, analog, or prodrug thereof (e.g., <image placeholder> ).

In embodiments, the terpene is a tirotundin or a derivative, analog, or prodrug thereof

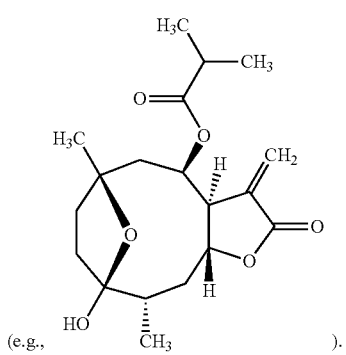 [SMILES: C=C1C(=O)O[C@@H]2C[C@H](C)[C@]3(O)CC[C@](C)(C[C@@H](OC(=O)C(C)C)[C@@H]12)O3]

In embodiments, the terpene is a clovane or a derivative, analog, or prodrug thereof

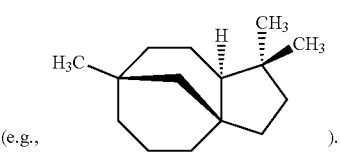

In embodiments, the terpene is a germacrane or a derivative, analog, or prodrug thereof

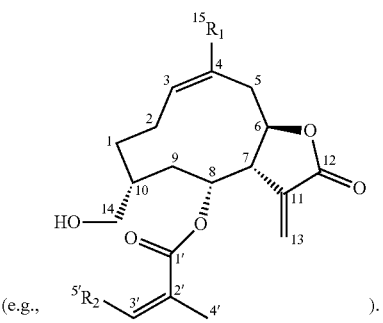

wherein $R_1$ is a moiety selected from —H, —OH, and —$CH_3$ and $R_2$ is a moiety selected from —$CH_3$.

In embodiments, the terpene is a sesterterpene or a derivative, analog, or prodrug thereof

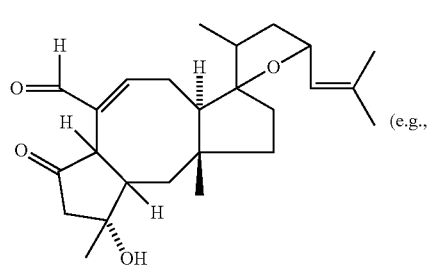

Ophiobolin A

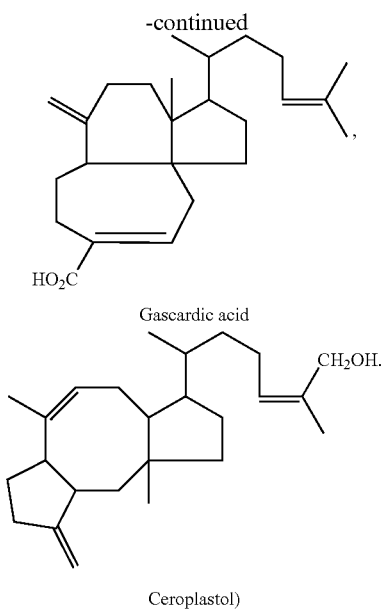

Gascardic acid

Ceroplastol)

In embodiments, the terpene is a triterpene or a derivative, analog, or prodrug thereof

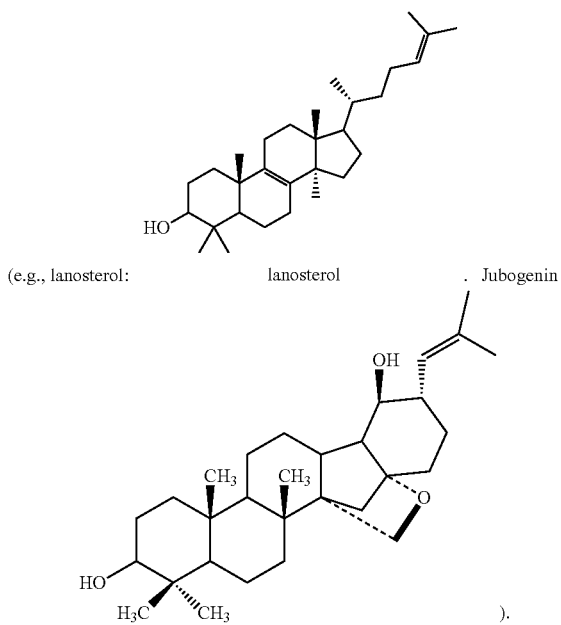

(e.g., lanosterol:    lanosterol    . Jubogenin    ).

The term "humulone" (or α-lupulic acid) refers to a prevalent member of the class of compounds known as alpha acids, which provide a characteristically bitter flavor. Humulone is a phloroglucinol derivative with three isoprenoid side-chains. Two side-chains are prenyl groups and one is an isovaleryl group. The acidity of the ring enol moieties that give rise to its designation as an acid lie in the vinylogous relationship with the ring and side chain carbonyl functional groups.

The term "humulene" (also known as α-humulene or α-caryophyllene), refers to a monocyclic sesquiterpene ($C_{15}H_{24}$), containing an 11-membered ring and consisting of three isoprene units containing three non-conjugated C=C double bonds, two of them being triply substituted and one being doubly substituted. It is found in the essential oils of Humulus lupulus. Humulene is an isomer of β-caryophyllene, and the two are often found together as a mixture in many aromatic plants.

The term "caryophyllene" (or (–)-β-caryophyllene), refers to a bicyclic sesquiterpene that is a constituent of many essential oils, especially clove oil, the oil from the stems and flowers of Syzygium aromaticum (cloves), the essential oil of Cannabis sativa, rosemary, and hops. It is usually found as a mixture with isocaryophyllene (the cis double bond isomer) and α-humulene. Caryophyllene possesses both a cyclobutane ring and as a trans-double bond in an 8-membered ring.

The term "lupulone" (or β-lupulic acid) refers to a beta acid found in Humulus lupulus (Hops). Lupulones are sensitive to oxidative decomposition; their break down creates flavors that may adversely affect the taste of beer.

The term "myrcene" (or β-myrcene) refers to an olefinic organic hydrocarbon, classified as a monoterpene. It is a component of the essential oil of several plants including bay, cannabis, ylang-ylang, wild thyme, parsley, and hops.

The term "alkaloid" refers to a group of naturally occurring chemical compounds that mostly contain basic nitrogen atoms. This group also includes some related compounds with neutral and even weakly acidic properties. In addition to carbon, hydrogen and nitrogen, alkaloids may also contain oxygen, sulfur, chlorine, bromine, and phosphorus. Alkaloids are produced by a large variety of organisms including bacteria, fungi, plants, and animals.

The term "cannabinoid" refers to a class of chemical compounds that act on cannabinoid receptors. These are G-protein-coupled receptors denoted by the terms $CB_1$ and $CB_2$ receptors. The structure of the CB1 receptor has been determined; see Hua, T., Vemuri, K., Pu, M., Qu, L., Han, G. W., Wu, Y., Zhao, S., Shui, W., Li, S., Korde, A. and Laprairie, R. B., 2016. Crystal structure of the human cannabinoid receptor CB 1. Cell, 167(3), pp. 750-'762, which is incorporated herein by reference for all purposes. The anatomical distribution of these receptors is complex, but broadly CB1 receptors in the central nervous system mediate many of the effects of cannabinoids in the brain, whereas CB2 receptors in the periphery mediate anti-inflammatory and related actions of cannabinoids. See Munro, S., Thomas, K. L. and Abu-Shaar, M., 1993. Molecular characterization of a peripheral receptor for cannabinoids. Nature, 365(6441), p. 61. which is incorporated herein by reference for all purposes There are at least 113 different cannabinoids isolated from cannabis, exhibiting varied effects. Many of these compounds are structurally related to Δ9-tetrahydrocannabinol (THC). Classes of natural cannabinoids isolated from cannabis include cannabigerol, cannabichromene, cannabidiol, tetrahydrocannabinol, cannabinol, cannabielsoin, iso-tetrahydrocannabinol, cannabicyclol, and cannabicitran. Examples of well-studied cannabinoids include cannabinol (CBN), tetrahydrocannabinol (THC), and cannabinol (CBN).

II. Methods

The methods provided herein include processes, methods, and compositions for the extraction of natural products from plant material employing pure fluorocarbon liquids or gases and optionally admixtures of fluorocarbon and non-fluorocarbon gases and liquids. In some embodiments, the extraction may be carried out in a highly selective manner such that specific components consisting of pure compounds or defined mixtures thereof may be extracted from plant or animal material without extracting undesired materials, obviating the need for subsequent purification steps following the extraction, wherein said specific components are valuable in the preparation of pharmaceutical and nutraceutical compositions which are useful in the prevention and treatment of various diseases and syndromes in humans and animals.

In a first aspect, is provided a method of extracting a natural organic compound from a natural material, the method including contacting the natural material with an extraction fluid thereby extracting the natural organic compound from the natural material into the extraction fluid to from an extracted fluid solution. In an embodiment, the extraction fluid includes a fluorophilic compound and a hydrofluorocarbon. In another embodiment, the extraction fluid is a non-ideal fluid.

In one embodiment, the natural material is a material derived from a plant, an animal, a fungi, a bacteria or a virus. In another embodiment, the natural material is a material derived from a plant. In another embodiment, the natural material is a material derived from an animal. In another embodiment, the natural material is a material derived from a fungus. In another embodiment, the natural material is a material derived from a bacteria. In another embodiment, the natural material is a material derived from a virus.

In one embodiment, the plant is *Piper methysticum, Cannabis* spp., *Salvia* spp., *Banisteriopsis caapi, Psychotria viridis* (chacruna), *Diplopterys cabrerana, Peganum harmala, Humulus lupulus* or mixture thereof. In another embodiment, the plant is *Piper methysticum*. In another embodiment, the plant is *Cannabis* spp. In another embodiment, the plant is *Salvia* spp. In another embodiment, the plant is *Banisteriopsis caapi*. In another embodiment, the plant is *Psychotria viridis* (chacruna). In another embodiment, the plant is *Diplopterys cabrerana*. In another embodiment, the plant is *Peganum harmala*. In another embodiment, the plant is *Humulus lupulus*. In another embodiment, the *Cannabis* spp. plant is *Cannabis Sativa*.

In one embodiment, the plant is *Echinacea purpurea, Echinacea angustifolia, Acmella oleracea, Helichrysum umbraculigerum,* or *Radula marginata*. In another embodiment the plant is an *Echinacea* spp. In another embodiment, the plant is *Echinacea purpurea*. In another embodiment, the plant is *Echinacea angustifolia*. In another embodiment, the plant is *Acmella oleracea*. In another embodiment, the plant is *Helichrysum umbraculigerum*. In another embodiment, the plant is *Radula marginata*.

In one embodiment, the natural organic compound is a biologically active organic compound. In another embodiment, the natural organic compound is an aromatic compound. In another embodiment, the natural organic compound forms part of an aromatic oil or essential oil. In another embodiment, the natural organic compound forms an aromatic oil. In another embodiment, the natural organic compound forms an essential oil. In another embodiment, the natural organic compound is a component of an aromatic oil. In another embodiment, the natural organic compound is a component of an essential oil. In another embodiment, the natural organic compound is caffeine. In one embodiment, the natural organic compound is a terpene, a humulone, a lupulone, a myrcene, a humulene, a caryophyllene, an alkaloid, a flavonoid, a cannabinoid, menthol, capsaicin, anise or camphor. In another embodiment, the natural organic compound is a terpene. In another embodiment, the natural organic compound is a humulone. In another embodiment, the natural organic compound is a lupulone. In another embodiment, the natural organic compound is a myrcene. In another embodiment, the natural organic compound is a humulene. In another embodiment, the natural organic compound is a caryophyllene. In another embodiment, the natural organic compound is an alkaloid. In another embodiment, the natural organic compound is a flavonoid. In another embodiment, the natural organic compound is menthol. In another embodiment, the natural organic compound is capsaicin. In another embodiment, the natural organic compound is anise. In another embodiment, the natural organic compound is camphor. In one embodiment, the natural organic compound is xanthohumol, 8-prenylnaringenin or isoxanthohumol. In another embodiment, the natural organic compound is xanthohumol. In another embodiment, the natural organic compound is 8-prenylnaringenin. In another embodiment, the natural organic compound is isoxanthohumol. In another embodiment, the natural organic compound is a prenylflavonoid. In another embodiment, the natural organic compound is a kavalactone or a salvorin.

In one embodiment, the natural organic compound is a cannibinoid. In another embodiment, the natural organic compound is tetrahydrocannabinol, cannabidiol or cannabinol. In another embodiment, the natural organic compound is cannabidiol. In another embodiment, the natural organic compound is cannabinol. In another embodiment, the natural organic compound is tetrahydrocannabinol.

In another embodiment, the natural organic compound is cannabigerol, cannabichromene, cannabicyclol, cannabivarin, tetrahydrocannabivarin, cannabidivarin, cannabichromevarin, cannabigerovarin, cannabigerol monomethyl ether, tetrahydrocannbinolic acid, or cannabidiolic acid. In another embodiment, the natural organic compound is cannabigerol. In another embodiment, the natural organic compound is cannabichromene. In another embodiment, the natural organic compound is cannabicyclol. In another embodiment, the natural organic compound is cannabivarin. In another embodiment, the natural organic compound is tetrahydrocannabivarin. In another embodiment, the natural organic compound is cannabidivarin. In another embodiment, the natural organic compound is cannabichromevarin. In another embodiment, the natural organic compound is cannabigerovarin. In another embodiment, the natural organic compound is cannabigerol monomethyl ether. In another embodiment, the natural organic compound is tetrahydrocannbinolic acid. In another embodiment, the natural organic compound is cannabidiolic acid.

In embodiments, at least 20 Kg of the natural organic compound is present in the extracted fluid solution. In embodiments, at least 10 Kg of the natural organic compound is present in the extracted fluid solution. In embodiments, at least 5 Kg of the natural organic compound is present in the extracted fluid solution. In embodiments, at least 4 Kg of the natural organic compound is present in the extracted fluid solution. In embodiments, at least 3 Kg of the natural organic compound is present in the extracted fluid solution. In embodiments, at least 2 Kg of the natural organic compound is present in the extracted fluid solution. In embodiments, at least 1 Kg of the natural organic compound is present in the extracted fluid solution. In embodiments, at least 500 g of the natural organic compound is present in the extracted fluid solution. In embodiments, at least 400 g of the natural organic compound is present in the extracted fluid solution. In embodiments, at least 300 g of the natural organic compound is present in the extracted fluid solution. In embodiments, at least 200 g of the natural organic compound is present in the extracted fluid solution.

In embodiments, at least 100 g of the natural organic compound is present in the extracted fluid solution. In embodiments, about 20 Kg of the natural organic compound is present in the extracted fluid solution. In embodiments, about 10 Kg of the natural organic compound is present in the extracted fluid solution. In embodiments, about 5 Kg of the natural organic compound is present in the extracted fluid solution. In embodiments, about 4 Kg of the natural organic compound is present in the extracted fluid solution. In embodiments, about 3 Kg of the natural organic compound is present in the extracted fluid solution. In embodiments, about 2 Kg of the natural organic compound is present in the extracted fluid solution. In embodiments, about 1 Kg of the natural organic compound is present in the extracted fluid solution. In embodiments, about 500 g of the natural organic compound is present in the extracted fluid solution. In embodiments, about 400 g of the natural organic compound is present in the extracted fluid solution. In embodiments, about 300 g of the natural organic compound is present in the extracted fluid solution. In embodiments, about 200 g of the natural organic compound is present in the extracted fluid solution. In embodiments, about 100 g of the natural organic compound is present in the extracted fluid solution. In embodiments, about 100 g to about 15 Kg of the natural organic compound is present in the extracted fluid solution. In embodiments, about 100 g to about 10 Kg of the natural organic compound is present in the extracted fluid solution. In embodiments, about 100 g to about 5 Kg of the natural organic compound is present in the extracted fluid solution. In embodiments, about 100 g to about 1 Kg of the natural organic compound is present in the extracted fluid solution. In embodiments, about 500 g to about 15 Kg of the natural organic compound is present in the extracted fluid solution. In embodiments, about 1 Kg to about 10 Kg of the natural organic compound is present in the extracted fluid solution. In embodiments, about 1 Kg to about 5 Kg of the natural organic compound is present in the extracted fluid solution.

In embodiments, the extraction fluid does not include supercritical $CO_2$. In embodiments, extraction fluid does not include argon. In embodiments, the extraction fluid does not include xenon. In embodiments, the extraction fluid does not include nitrous oxide.

In an embodiment, the extraction fluid includes trifluoroethanol or hexafluoroisopropanol. In an embodiment, the extraction fluid includes trifluoroethanol. In an embodiment, the extraction fluid includes hexafluoroisopropanol.

In embodiments, the extraction fluid is above about 15° C. In embodiments, the extraction fluid is above about 20° C. In embodiments, the extraction fluid is from about 15° C. to about 35° C. In embodiments, the extraction fluid is from about 20° C. to about 30° C. In embodiments, the extraction fluid is about 15° C. In embodiments, the extraction fluid is about 16° C. In another embodiment, the extraction fluid is about 17° C. In another embodiment, the extraction fluid is about 18° C. In another embodiment, the extraction fluid is about 19° C. In another embodiment, the extraction fluid is about 20° C. In another embodiment, the extraction fluid is about 21° C. In another embodiment, the extraction fluid is about 22° C. In another embodiment, the extraction fluid is about 23° C. In another embodiment, the extraction fluid is about 24° C. In another embodiment, the extraction fluid is about 25° C. In another embodiment, the extraction fluid is about 26° C. In another embodiment, the extraction fluid is about 27° C. In another embodiment, the extraction fluid is about 28° C. In another embodiment, the extraction fluid is about 29° C. In another embodiment, the extraction fluid is about 30° C. In another embodiment, the extraction fluid is about 31° C. In another embodiment, the extraction fluid is about 32° C. In another embodiment, the extraction fluid is about 33° C. In another embodiment, the extraction fluid is about 34° C. In another embodiment, the extraction fluid is about 35° C.

In one embodiment, the hydrofluorocarbon is a hydrofluoroether, a hydrofluoroketone, a hydrofluoroaromatic or a hydrofluoroolefin. In another embodiment, the hydrofluorocarbon is a hydrofluoroether. In another embodiment, the hydrofluorocarbon is a hydrofluoroketone. In another embodiment, the hydrofluorocarbon is a hydrofluoroaromatic. In another embodiment, the hydrofluorocarbon is a hydrofluoroolefin.

In one embodiment, the hydrofluorocarbon is chlorodifluoromethane, methyl nonafluoroisobutyl ether, methyl nonafluorobutyl ether, ethyl nonafluoroisobutyl ether, ethyl nonafluorobutyl ether, 3-ethoxy-1,1,1,2,3,4,4,5,5,6,6,6-dodecafluoro-2-trifluoromethylhexane.trifluoromethane (HFC-23), difluoromethane (HFC-32), pentafluoroethane (HFC-125), 1,1,2,2-tetrafluoroethane (HFC-134), 1,1,1,2-tetrafluoroethane (HFC-134a), 1,1,1-trifluoroethane (HFC-143a), 1,1-difluoroethane (HFC-152a) or fluoroethane (HFC-161). In another embodiment, the hydrofluorocarbon is chlorodifluoromethane. In another embodiment, the hydrofluorocarbon is methyl nonafluoroisobutyl ether. In another embodiment, the hydrofluorocarbon is methyl nonafluorobutyl ether. In another embodiment, the hydrofluorocarbon is ethyl nonafluoroisobutyl ether. In another embodiment, the hydrofluorocarbon is ethyl nonafluorobutyl ether. In another embodiment, the hydrofluorocarbon is 3-ethoxy-1,1,1,2,3,4,4,5,5,6,6,6-dodecafluoro-2-trifluoromethylhexane.trifluoromethane (HFC-23). In another embodiment, the hydrofluorocarbon is difluoromethane (HFC-32). In another embodiment, the hydrofluorocarbon is pentafluoroethane (HFC-125). In another embodiment, the hydrofluorocarbon is 1,1,2,2-tetrafluoroethane (HFC-134). In another embodiment, the hydrofluorocarbon is 1,1,1,2-tetrafluoroethane (HFC-134a). In another embodiment, the hydrofluorocarbon is 1,1,1-trifluoroethane (HFC-143a). In another embodiment, the hydrofluorocarbon is 1,1-difluoroethane (HFC-152a). In another embodiment, the hydrofluorocarbon is fluoroethane (HFC-161).

In one embodiment, the fluorophilic compound is dimethyl ether.

In one embodiment, the method includes, prior to contacting, freezing the natural material at a temperature from about 0° C. to about −60° C. (e.g., at about 0 to −50, 0 to −40, 0 to −30, 0 to −20, 0 to −10, 0, −1, −2, −3, −4, −5, −6, −7, −8, −9, −10, −15, −20, −25, −30, −35, −40, −45, or −50° C.). In embodiments, freezing the natural material uses a freezer. In embodiments, freezing the natural material uses a blast freezer. In embodiments, freezing the natural material uses compressed cryogenic gas (e.g., $CO_2$, $N_2$, He). In another embodiment, the mole fraction of the fluorophilic compound is at least four-fold (e.g., at least 5-fold, 6-fold, 7-fold, 8-fold, 9-fold, 10-fold, 15-fold, 20-fold, or 25-fold) greater than the mole fraction of the hydrofluorocarbon. In embodiments, the method includes a recirculating pump to administer the extraction fluid to the natural material. In embodiments, the method includes volatilizing the extraction fluid. In embodiments, the natural organic compound is not volatilized when the extraction fluid is volatilized. In embodiments, the method includes extracting the volatilized extraction fluid. In embodiments, the method includes chilling the extracted volatilized extraction fluid (e.g., with a heat exchanger). In embodiments, the method includes compressing the chilled extracted volatilized extraction fluid (e.g., to an extraction liquid). In embodiments, the method includes warming the extraction liquid resulting from chilling the extracted volatilized extraction fluid. In embodiments the method includes recirculating the warmed extraction liquid resulting from chilling the extracted volatilized extraction fluid (e.g. continuously for a fixed amount of time). In embodiments the method includes warming the recirculated extraction fluid to a temperature range from about 40° C. to about 80° C. (e.g., to about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80° C.). In embodiments the method includes warming the recirculated extraction fluid to a temperature of about 80° C. In embodiments the method includes collecting portions of the recirculating extraction fluid while warming the recirculating extraction fluid to a temperature of about 80° C. (e.g., from 40 to 80° C.). In another embodiment, the method includes separating the extraction fluid from the natural material by volatizing the extraction fluid to form a volatilized extraction fluid. In another embodiment, the method includes chilling and compressing the volatilized extraction fluid to form a liquid extraction fluid. In another embodiment, the method includes recirculating the liquid extraction fluid to the natural material. In another embodiment, the method includes collecting separated fractions of the liquid extraction fluid. In embodiments, extraction fluid includes a mole fraction of a fluorocarbon at least four-fold (e.g., at least 5-fold, 6-fold, 7-fold, 8-fold, 9-fold, 10-fold, 15-fold, 20-fold, or 25-fold) greater than the mole fraction of the hydrofluorocarbon. In embodiments, extraction fluid includes an additional component (e.g., fluorophilic compound, fluorophilic amine, alocohol, or non-fluorinated hydroxy-alkyl, non-fluorinated hydroxy-cycloalkyl, or non-fluorinated hydroxyl-aryl, inert gas (e.g., $SF_6$, $CO_2$, $N_2O$, $CH_4$, $C_2H_6$, argon)). In embodiments, the mole fraction of the additional component of the extraction fluid is at least four fold (e.g., at least 5-fold, 6-fold, 7-fold, 8-fold, 9-fold, 10-fold, 15-fold, 20-fold, or 25-fold) less than the mole fraction of the hydrofluorocarbon.

In an aspect, is provided a fluid including chlorodifluoromethane and dimethylether. In one embodiment, the fluid is a non-ideal fluid.

In an aspect is provided an apparatus for the extraction of natural products (e.g., of medicinal, nutraceutical, health-promoting, or pharmacological, or other value) from a plant, animal, bacterial, fungal, or viral material, or mixtures thereof (e.g., which contain multiple natural products). In embodiments, the desired materials are separated from the undesired materials (e.g., leaving the undesired materials in the unextracted residue. In embodiments, the apparatus frees the desired material in solution. In embodiments, the natural product is further purified (e.g., by fractional distillation, flash chromatography, preparative high pressure liquid chromatography on normal and reverse phase media, countercurrent liquid chromatography, liquid-liquid extraction, co-solvent precipitation, or crystallization).

In an aspect is provided a method (process) for the extraction of natural products (e.g., of medicinal, nutraceutical, health-promoting, or pharmacological, or other value) from a plant, animal, bacterial, fungal, or viral material, or mixtures thereof (e.g., which contain multiple natural products). In embodiments, the desired materials are separated from the undesired materials (e.g., leaving the undesired materials in the unextracted residue. In embodiments, the apparatus frees the desired material in solution. In embodiments, the natural product is further purified (e.g., by fractional distillation, flash chromatography, preparative high pressure liquid chromatography on normal and reverse phase media, countercurrent liquid chromatography, liquid-liquid extraction, co-solvent precipitation, or crystallization).

In as aspect is provided a composition for the extraction of natural products (e.g., of medicinal, nutraceutical, health-promoting, or pharmacological, or other value) from a plant, animal, bacterial, fungal, or viral material, or mixtures thereof (e.g., which contain multiple natural products). In embodiments, the desired materials are separated from the undesired materials (e.g., leaving the undesired materials in the unextracted residue. In embodiments, the apparatus frees the desired material in solution. In embodiments, the natural product is further purified (e.g., by fractional distillation, flash chromatography, preparative high pressure liquid chromatography on normal and reverse phase media, countercurrent liquid chromatography, liquid-liquid extraction, co-solvent precipitation, or crystallization).

In embodiments, the composition includes a hydrofluorocarbon or fluorocarbon. In embodiments, the composition includes a hydrofluorocarbon and fluorocarbon. In embodiments, the composition includes a hydrofluorocarbon. In embodiments, the composition includes a fluorocarbon. In some embodiments, the composition includes hydrofluorocarbons, fluorocarbons, and optionally other substances selected from the alkanes, alkenes, alkynes, alcohols, and aromatic hydrocarbons. In embodiments, the composition includes at least one fluorocarbon which is Freon™ 134a (1,1,1,2-Tetrafluoroethane).

In embodiments, the method of extraction includes fractional distillation, flash chromatography, preparative high pressure liquid chromatography on normal and reverse phase media, countercurrent liquid chromatography, liquid-liquid extraction, co-solvent precipitation, crystallization, or combinations thereof. In embodiments, the method of extraction includes fractional distillation. In embodiments, the method of extraction includes flash chromatography. In embodiments, the method of extraction includes preparative high pressure liquid chromatography on normal and reverse phase media. In embodiments, the method of extraction includes fractional distillation, countercurrent liquid chromatography. In embodiments, the method of extraction includes liquid-liquid extraction. In embodiments, the method of extraction includes co-solvent precipitation. In embodiments, the method of extraction includes crystallization. Instruments for extraction may include mass spectrometer (MS), gas chromatograph (GC), GC-mass spectrometer, liquid chromatography mass spectrometer, high pressure liquid chromatograph, and combinations thereof.

Described herein is a multiplicity of co-solvents, provided that the principal extraction medium is either a fluorocarbon or a hydrofluorocarbon in admixture with another fluorophilic compound. Mixtures of fluorocarbons, hydrofluorocarbons, and optionally alkanes, including but not limited to straight chain, branched chain, cycloalkanes, and alkylcycloalkanes, possess the previously unexpected ability to extract specific components of high commercial and health-related value from plant, animal, fungi, bacteria, or virus material. In some embodiments, solvents useful in the methods of the present invention include fluorocarbons and hydrofluorocarbons. Furthermore, forming the continuous phase from mixtures of fluorocarbons is also contemplated herein. In embodiments, the instant conversion of a discontinuous phase to a continuous phase represents the conditions where the maximum solubility of desired, highly hydrophobic plant, animal, fungi, bacteria, or virus materials may be maximally evidenced.

In embodiments, the extraction fluid (e.g. including extraction components) includes trifluorethanol. In embodiments, the extraction fluid (e.g. including extraction components) includes hexafluoroisopropanol. In embodiments, the extraction fluid (e.g. including extraction components) includes chlorodifluoromethane and dimethylether. In embodiments, the extraction fluid (e.g. including extraction components) includes chlorodifluoromethane. In embodiments, the extraction fluid (e.g. including extraction components) includes dimethylether. In embodiments, the extraction fluid (e.g. including extraction components) includes a liquid-gas mixture. In embodiments, the extraction fluid (e.g. including extraction components) is a non-ideal fluid. In embodiments, extraction fluid (e.g. including extraction components) does not include supercritical $CO_2$, argon, xenon, or nitrous oxide. In embodiments, extraction fluid (e.g. including extraction components) does not include supercritical $CO_2$. In embodiments, extraction fluid (e.g. including extraction components) does not include argon. In embodiments, extraction fluid (e.g. including extraction components) does not include xenon. In embodiments, extraction fluid (e.g. including extraction components) does not include nitrous oxide. In embodiments, the extraction fluid (e.g. including extraction components) includes a hydrofluorocarbon In some embodiments, the extraction fluid includes a hydrofluorocarbon and a fluorophilic compound. The hydrofluorocarbon may include but is not limited to: a hydrofluoroether, a hydrofluoroketone, a hydrofluoroaromatic or a hydrofluoroolefin, chlorodifluoromethane, methyl nonafluoroisobutyl ether, methyl nonafluorobutyl ether, ethyl nonafluoroisobutyl ether, ethyl nonafluorobutyl ether, 3-ethoxy-1,1,1,2,3,4,4,5,5,6,6,6-dodecafluoro-2-trifluoromethylhexane.trifluoromethane (HFC-23), difluoromethane (HFC-32), pentafluoroethane (HFC-125), 1,1,2,2-tetrafluoroethane (HFC-134), 1,1,1,2-tetrafluoroethane (HFC-134a), 1,1,1-trifluoroethane (HFC-143a), 1,1-difluoroethane (HFC-152a) or fluoroethane (HFC-161). The fluorophilic compound may include dimethyl ether.

In some embodiments, the mole fraction of the fluorophilic compound is at least four-fold greater than the mole fraction of the hydrofluorocarbon. The mole fraction of the fluorophilic compound may be at least four fold greater, five-fold greater, six fold greater, seven fold greater, eight fold greater, nine fold greater, ten-fold greater, twenty fold greater, fifty fold greater, seventy five-fold greater, or one hundred fold greater than the mole fraction of the hydrofluorocarbon.

In some embodiments, the mole fraction of dimethyl ether is at least four-fold greater than the mole fraction of the chlorodifluoromethane. The mole fraction of dimethyl ether may be at least four fold greater, five-fold greater, six fold greater, seven fold greater, eight fold greater, nine fold greater, ten-fold greater, twenty fold greater, fifty fold greater, seventy five-fold greater, or one hundred fold greater than the mole fraction of the chlorodifluoromethane.

In some embodiments, the extraction fluid is above about 15° C. In embodiments, the extraction fluid is above about 20° C. In embodiments, the extraction fluid is from about 15° C. to about 35° C. In embodiments, the extraction fluid is from about 20° C. to about 30° C. In embodiments, the extraction fluid is above about 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., or 35° C. In some embodiments, the extraction fluid is above 15° C. In embodiments, the extraction fluid is above 20° C. In embodiments, the extraction fluid is from 15° C. to 35° C. In embodiments, the extraction fluid is from 20° C. to 30° C. In embodiments, the extraction fluid is above 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., or 35° C.

In embodiments, an ionic liquid includes a cation described by one or more of the following formulae:

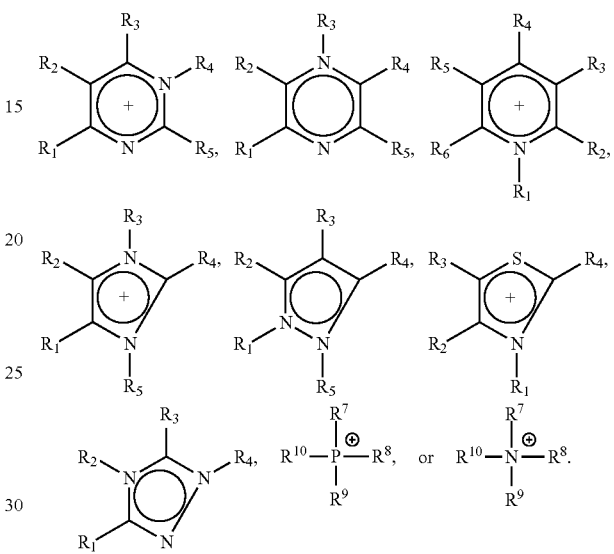

$R_1$, $R_2$, $R_3$, $R_4$, $R_5$, $R_6$, $R^7$, $R^8$, $R^9$, and $R^{10}$ are independently halogen, $-CX_3$, $-CHX_2$, $-CH_2X$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCX_3$, $-OCHX_2$, $-OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. Two of $R_1$, $R_2$, $R_3$, $R_4$, $R_5$, $R_6$, $R^7$, $R^8$, $R^9$, and $R^{10}$ may independently optionally be joined to form a substituted or unsubstituted cycloalkyl, substituted or unsubstituted heterocycloalkyl, substituted or unsubstituted aryl, substituted or unsubstituted heteroaryl.

In embodiments, $R_1$, $R_2$, $R_3$, $R_4$, $R_5$, $R_6$, $R^7$, $R^8$, $R^9$, and $R^{10}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, two of $R_1$, $R_2$, $R_3$, $R_4$, $R_5$, $R_6$, $R^7$, $R^8$, $R^9$, and $R^{10}$ may independently optionally be joined to form a substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, wherein $R^1$, $R^2$, $R^3$, $R^4$, $R^5$ and $R^6$ are each independently selected from the group consisting of: (i) H; (ii) halogen; (iii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH; (iv) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, NH2 and SH; (v) $C_6$ to $C_{20}$ unsubstituted aryl, or $C_3$ to $C_{25}$ unsubstituted heteroaryl having one to three heteroatoms independently selected from the group consisting of O, N, Si and S; and (vi) $C_6$ to $C_{25}$ substituted aryl, or $C_3$ to $C_{25}$ substituted heteroaryl having one to three heteroatoms independently selected from the group consisting of O, N, Si and S; wherein said substituted aryl or substituted heteroaryl has one to three substituents independently selected from the group consisting of: 1. —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH, 2. OH, 3. $NH_2$, and 4. SH. In embodiments, $R^7$, $R^8$, $R^9$, and $R^{10}$ are each independently selected from the group consisting of: (vii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH; (viii) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH; (ix) $C_6$ to $C_{25}$ unsubstituted aryl, or $C_3$ to $C_{25}$ unsubstituted heteroaryl having one to three heteroatoms independently selected from the group consisting of O, N, Si and S; and (x) $C_6$ to $C_{25}$ substituted aryl, or $C_3$ to $C_{25}$ substituted heteroaryl having one to three heteroatoms independently selected from the group consisting of O, N, Si and S; wherein said substituted aryl or substituted heteroaryl has one to three substituents independently selected from the group consisting of: (1) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $MI_2$ and SH, (2) OH, (3) $NH_2$, and (4) SH; and wherein optionally at least two of $R^1$, $R^2$, $R^3$, $R^4$, $R^5$, $R^6$, $R^7$, $R^8$, $R^9$, and $R^{10}$ can together form a cyclic or bicyclic alkanyl or alkenyl group. In embodiments, an ionic liquid includes fluorinated cations wherein at least one member selected from $R^1$, $R^2$, $R^3$, $R^4$, $R^5$, $R^6$, $R^7$, $R^8$, $R^9$, and $R^{10}$, as described above, includes F.

In embodiments, is included the extraction of medicinally, pharmaceutically, or other economically valuable organic compounds, including but not limited to terpenes, alkaloids, and essential oils (e.g., for preparation of flavors and fragrances). In embodiments, the extraction includes use of two different fluorophilic compounds, specifically a fluorocarbon and a hydrofluorocarbon. In embodiments, is included the extraction of medicinally, pharmaceutically, or other economically valuable organic compounds, including but not limited to terpenes, alkaloids, and essential oils (e.g., for preparation of flavors and fragrances). In embodiments, the extraction includes use of three different chemical compounds, including two different fluorophilic compounds (e.g., a fluorocarbon and a hydrofluorocarbon), and an alkane. In embodiments, is included the extraction of medicinally, pharmaceutically, or other economically valuable organic compounds, including but not limited to terpenes, alkaloids, and essential oils (e.g., for preparation of flavors and fragrances). In embodiments, the extraction includes use of three different fluorophilic chemical compounds, including two different fluorophilic compounds (e.g., a fluorocarbon and a hydrofluorocarbon), and a fluorinated ether. In some embodiments, the mixture is a fluorocarbon and an ionic liquid.

In embodiments, a natural organic compound is extracted from a natural material (e.g., plant, animal, fungi, bacteria, or virus). In embodiments, the natural material is a plant. In embodiments, the plant is *Piper methysticum, Cannabis* spp., *Salvia* spp., *Banisteriopsis caapi, Psychotria viridis* (chacruna), *Diplopterys cabrerana, Peganum harmala, Humulus lupulus* or mixtures thereof.

In some embodiments, are methods of extracting natural organic compounds from natural materials. In some embodiments, natural organic compound includes biologically active organic compound. In some embodiments, the natural organic compound includes aromatic oil and/or essential oil. In embodiments, the natural organic compound is caffeine, terpene, a humulone, a lupulone, a myrcene, a humulene, a caryophyllene, an alkaloid, a flavonoid, a cannabinoid, menthol, capsaicin, anise, camphor, xanthohumol, 8-prenylnaringenin, isoxanthohumol, prenylflavonoid, kavalactone, or a salvorin. In embodiments, the natural product is cannabinoid. In embodiments, the cannabinoid is tetrahydrocannabinol, cannabidiol, or cannabinol. In embodiments, the natural organic compound is tetrahydrocannabinol.

In embodiments, the plant, animal, fungi, bacteria, or virus material used is cannabis. Multiple medicinal uses have been found for the active ingredients of cannabis, either *Cannabis* spp. but most commonly *Cannabis sativa*. Other plants than *Cannabis* spp. may contain useful cannabinoid activity, or may possess compounds, typically terpeneoid in character, which possess micromolar or higher affinity for the $CB_1$ or $CB_2$ cannabinoid receptors present in a man, animal, or bird.

Cannabinoids present in cannabis include the ingredients tetrahydrocannabinol, cannabinol, cannabidiol, and cannabichromene. The medicinal uses of cannabis include but are not limited to: epilepsy [Porter, Brenda E., and Catherine Jacobson. "Report of a parent survey of cannabidiol-enriched cannabis use in pediatric treatment-resistant epilepsy." *Epilepsy & Behavior* 29, no. 3 (2013): 574-577, which is incorporated herein by reference for all purposes]; pain [Cooper, Ziva D., Sandra D. Comer, and Margaret Haney. "Comparison of the analgesic effects of dronabinol and smoked marijuana in daily marijuana smokers." *Neuropsychopharmacology* 38, no. 10 (2013): 1984-1992; Kahan, Meldon, Anita Srivastava, Sheryl Spithoff, and Lisa Bromley. "Prescribing smoked cannabis for chronic noncancer pain Preliminary recommendations." *Canadian Family Physician* 60, no. 12 (2014): 1083-1090; Wilsey, Barth, Thomas Marcotte, Reena Deutsch, Ben Gouaux, Staci Sakai, and Haylee Donaghe. "Low-dose vaporized cannabis significantly improves neuropathic pain." *The Journal of Pain* 14, no. 2 (2013): 136-148, which are incorporated herein by reference for all purposes], specifically as evidenced in the treatment of nausea and pain associated with cancer and chemotherapy [United States Patent Document U.S. Pat. No. 8,119,697, Anti-Nausea and Anti Vomiting Activity of Cannabadiol Compounds, which is incorporated herein by reference for all purposes]; viral infection [Molina, Patricia E., Peter Winsauer, Ping Zhang, Edith Walker, Leslie Birke, Angela Amedee, Curtis Vande Stouwe et al. "Cannabinoid administration attenuates the progression of simian immunodeficiency virus." *AIDS research and human retroviruses* 27, no. 6 (2011): 585-592, which is incorporated herein by reference for all purposes]; AIDS-related pain and Wasting; multiple sclerosis [Svendsen, Kristina B., Troels S. Jensen, and Flemming W. Bach. "Does the cannabinoid dronabinol reduce central pain in multiple sclerosis? Randomized double blind placebo controlled crossover trial." *Bmj* 329, no. 7460 (2004): 253, which is incorporated herein by reference for all purposes] arthritis; rheumatism; glaucoma [Hingorani, Tushar, Waseem Gul, Mahmoud Elsohly, Michael A. Repka, and Soumyajit Majumdar. "Effect of ion pairing on in vitro transcorneal permeability of a Δ9-tetrahydrocannabinol prodrug: Potential in glaucoma therapy." *Journal of pharmaceutical sciences* 101, no. 2 (2012): 616-626, which is incorporated herein by reference for all purposes]; migraines; muscle spasticity; chemical dependency. Prior art further suggests that cannabis and its components have utility in oncology [Chakravarti, Bandana, Janani Ravi, and Ramesh K. Ganju. "Cannabinoids as therapeutic agents in cancer: current status and future implications." *Oncotarget* 5, no. 15 (2014): 5852], Parkinson's disease [see, for example, More, Sandeep Vasant, and Dong-Kug Choi. "Promising cannabinoid-based therapies for Parkinson's disease: motor symptoms to neuroprotection." *Molecular neurodegeneration* 10, no. 1 (2015): 1-26, which is incorporated herein by reference for all purposes], Within this embodiment, extracted material may be used as a composition to treat post-herpetic neuralgia, shingles, burns, actinic keratosis, oral cavity sores, oral ulcers, post-episiotomy pain, psoriasis, pruritus, contact dermatitis, eczema, bullous dermatitis herpetiformis, exfoliative dermatitis, mycosis fungoides, pemphigus, severe erythema multiforme, seborrheic dermatitis, psoriatic arthritis, diabetic neuropathy, ankylosing spondylitis, Reiter's syndrome, gout, chondrocalcinosis, joint pain secondary to dysmenorrhea, fibromyalgia [Fiz, Jimena, Marta Duran, Dolors Capella, Jordi Carbonell, and Magi Farr& "Cannabis use in patients with fibromyalgia: effect on symptoms relief and health-related quality of life." (2011): e18440, which is incorporated herein by reference for all purposes], musculoskeletal pain, neuropathic-postoperative complications, polymyositis, acute nonspecific tenosynovitis, bursitis, epicondylitis, post-traumatic osteoarthritis, synovitis, juvenile rheumatoid arthritis, contact eczema, allergies (not otherwise specified), phototoxic reactions, inflammatory and itching dermatoses, rosacea, perioral dermatitis, acne, acne, psoriasis, mosquito and other insect bites, skin atrophy, allergic rhinitis, conjunctivitis, otitis, bronchial asthma, Crohn's disease, ulcerative colitis, sarcoidosis, inflammatory-rheumatic diseases of the soft tissue or joints, mycoses, or combinations thereof.

In embodiments, the plant is *Cannabis* spp. In embodiments, the apparatus, method, or composition includes Freon™ 134a (1,1,1,2-Tetrafluoroethane). In embodiments, the apparatus, method, or composition includes Freon™ 134a (1,1,1,2-Tetrafluoroethane) and optionally one or more of carbon dioxide, nitrous oxide, sulfur hexafluoride, trifluoromethane, trifluoromethyl iodide, or tetrafluoromethane. In embodiments, the apparatus, method, or composition includes two extraction components (e.g., one component used in the extraction consists of Freon™ 134a (1,1,1,2-Tetrafluoroethane) and another is selected from the optional group of gases consisting of carbon dioxide, nitrous oxide, sulfur hexafluoride, trifluoromethane, trifluoromethyl iodide, or tetrafluoromethane; one component used in the extraction is Freon™ 134a (1,1,1,2-Tetrafluoroethane) within the range of 20 mol-% to 99 mol-% and another is selected from the optional group of gases consisting of carbon dioxide, nitrous oxide, sulfur hexafluoride, trifluoromethane, trifluoromethyl iodide, or tetrafluoromethane in the range independently from 80 mol-% to 1 mol-%; one component used in the extraction is Freon™ 134a (1,1,1,2-Tetrafluoroethane) within the range of 80 mol-% to 90 mol-% and another is selected from the optional group of gases consisting of carbon dioxide, nitrous oxide, sulfur hexafluoride, trifluoromethane, trifluoromethyl iodide, or tetrafluoromethane in the range independently from 10 mol-% to 20 mol-%; or one component used in the extraction consists of Freon™ 134a (1,1,1,2-Tetrafluoroethane) within the range of 80 mol-% to 90 mol-% and another is selected from the optional group of gases consisting of carbon dioxide, nitrous oxide, sulfur hexafluoride, trifluoromethane, trifluoromethyl iodide, or tetrafluoromethane in the range independently from 9 mol-% to 19 mol-% where ethanol is present in the range from 1 mol-% to 10 mol-%).

In embodiments, the plant material used is *Salvia* spp. Multiple medicinal uses have been found for the active ingredients of *Salvia* spp. in particular achieving sedation and tranquilization in psychiatric and neurological disorders and treatment of insomnia [see for example Perron, Brian E., Brian K. Ahmedani, Michael G. Vaughn, Joseph E. Glass, Arnelyn Abdon, and Li-Tzy Wu. "Use of Salvia divinorum in a nationally representative sample." *The American journal of drug and alcohol abuse* 38, no. 1 (2012): 108-113; Potter, David N., Diane Damez-Werno, William A. Carlezon, Bruce M. Cohen, and Elena H. Chartoff. "Repeated exposure to the κ-opioid receptor agonist salvinorin A modulates extracellular signal-regulated kinase and reward sensitivity." *Biological psychiatry* 70, no. 8 (2011): 744-753; Teksin, Zeynep S., Insong J. Lee, Noble N. Nemieboka, Ahmed A. Othman, Vijay V. Upreti, Hazem E. Hassan, Shariq S. Syed, Thomas E. Prisinzano, and Natalie D. Eddington. "Evaluation of the transport, in vitro metabolism and pharmacokinetics of Salvinorin A, a potent hallucinogen." *European Journal of Pharmaceutics and Biopharmaceutics* 72, no. 2 (2009): 471-477, which are incorporated herein by reference for all purposes]. Salvinorin A and other closely related salvinorins have substantial activity at the nanomolar level on kappa-type opioid receptors, which are involved, among other things, in analgesia. Accordingly, the extracts obtained from *Salvia* spp. are of utility of the treatment and amelioration of the disease process as well as the symptomatology of a variety diseases and pathological conditions, such as pain, especially neuropathic pain and cancer-breakthrough pain, which would normally be responsive to opioids.

In embodiments, the plant is *Salvia* spp. In embodiments, the apparatus, method, or composition includes Freon™ 134a (1,1,1,2-Tetrafluoroethane). In embodiments, the apparatus, method, or composition includes Freon™ 134a (1,1,1,2-Tetrafluoroethane) and optionally one or more of carbon dioxide, nitrous oxide, sulfur hexafluoride, trifluoromethane, trifluoromethyl iodide, or tetrafluoromethane. In embodiments, the apparatus, method, or composition includes two extraction components (e.g., one component used in the extraction is Freon™ 134a (1,1,1,2-Tetrafluoroethane) and another is selected from the optional group of gases consisting of carbon dioxide, nitrous oxide, sulfur hexafluoride, trifluoromethane, trifluoromethyl iodide, or tetrafluoromethane; one component used in the extraction is Freon™ 134a (1,1,1,2-Tetrafluoroethane) within the range of 20 mol-% to 99 mol-% and another is selected from the optional group of gases consisting of carbon dioxide, nitrous oxide, sulfur hexafluoride, trifluoromethane, trifluoromethyl iodide, or tetrafluoromethane in the range independently from 80 mol-% to 1 mol-%; one component used in the extraction is Freon™ 134a (1,1,1,2-Tetrafluoroethane) within the range of 80 mol-% to 90 mol-% and another is selected from the optional group of gases consisting of carbon dioxide, nitrous oxide, sulfur hexafluoride, trifluoromethane, trifluoromethyl iodide, or tetrafluoromethane in the range independently from 10 mol-% to 20 mol-%; one component used in the extraction is Freon™ 134a (1,1,1,2-Tetrafluoroethane) within the range of 80 mol-% to 90 mol-% and another is selected from the optional group of gases consisting of carbon dioxide, nitrous oxide, sulfur hexafluoride, trifluoromethane, trifluoromethyl iodide, or tetrafluoromethane in the range independently from 9 mol-% to 19 mol-% where ethanol is present in the range from 1 mol-% to 10 mol-%.

In embodiments, the plant material used is *Banisteriopsis caapi*, *Psychotria viridis* (chacruna), *Diplopterys cabrerana* (also known as chaliponga and chagropanga), *Peganum harmala*, or any mixture thereof. Multiple medicinal uses have been found for the active ingredients of *Banisteriopsis caapi*, *Psychotria viridis* (chacruna), *Diplopterys cabrerana* (also known as chaliponga and chagropanga), *Peganum harmala*, or any mixture thereof, in particular achieving sedation and tranquilization in psychiatric and neurological disorders and treatment of insomnia. See, for example, Riba, Jordi, Marta Valle, Gloria Urbano, Mercedes Yritia, Adelaida Morte, and Manel J. Barbanoj. "Human pharmacology of ayahuasca: subjective and cardiovascular effects, monoamine metabolite excretion, and pharmacokinetics." Journal of Pharmacology and Experimental Therapeutics 306, no. 1 (2003): 73-83; Rivier, Laurent, and Jan-Erik Lindgren. "'Ayahuasca,' the South American hallucinogenic drink: An ethnobotanical and chemical investigation." Economic Botany 26, no. 2 (1972): 101-129, which are incorporated herein by reference for all purposes. Accordingly, the extracts obtained from *Banisteriopsis caapi*, *Psychotria viridis* (chacruna), *Diplopterys cabrerana* (also known as chaliponga and chagropanga), *Peganum harmala*, or any mixture thereof. Such mixtures are of utility of the treatment and amelioration of the disease process as well as the symptomatology of the diseases and pathological conditions, especially in the treatment of psychiatric disorders, such as depression.

In embodiments, the plant is *Banisteriopsis caapi*, *Psychotria viridis* (chacruna), *Diplopterys cabrerana* (also known as chaliponga and chagropanga), *Peganum harmala*, or any mixture thereof. In embodiments, the plant is *Banisteriopsis caapi*. In embodiments, the plant is *Psychotria viridis* (chacruna). In embodiments, the plant is *Diplopterys cabrerana* (also known as chaliponga and chagropanga). In embodiments, the plant is *Peganum harmala*. In embodiments, the apparatus, method, or composition includes Freon™ 134a (1,1,1,2-Tetrafluoroethane). In embodiments, the apparatus, method, or composition includes Freon™ 134a (1,1,1,2-Tetrafluoroethane) and optionally one or more of carbon dioxide, nitrous oxide, sulfur hexafluoride, trifluoromethane, trifluoromethyl iodide, or tetrafluoromethane. In embodiments, the apparatus, method, or composition includes two extraction components (e.g., one component used in the extraction is Freon™ 134a (1,1,1,2-Tetrafluoroethane) and another is selected from the optional group of gases consisting of carbon dioxide, nitrous oxide, sulfur hexafluoride, trifluoromethane, trifluoromethyl iodide, or tetrafluoromethane; one component used in the extraction is Freon™ 134a (1,1,1,2-Tetrafluoroethane) within the range of 20 mol-% to 99 mol-% and another is selected from the optional group of gases consisting of carbon dioxide, nitrous oxide, sulfur hexafluoride, trifluoromethane, trifluoromethyl iodide, or tetrafluoromethane in the range independently from 80 mol-% to 1 mol-%; one component used in the extraction is Freon™ 134a (1,1,1,2-Tetrafluoroethane) within the range of 80 mol-% to 90 mol-% and another is selected from the optional group of gases consisting of carbon dioxide, nitrous oxide, sulfur hexafluoride, trifluoromethane, trifluoromethyl iodide, or tetrafluoromethane in the range independently from 10 mol-% to 20 mol-%; one component used in the extraction is Freon™ 134a (1,1,1,2-Tetrafluoroethane) within the range of 80 mol-% to 90 mol-% and another is selected from the optional group of gases consisting of carbon dioxide, nitrous oxide, sulfur hexafluoride, trifluoromethane, trifluoromethyl iodide, or tetrafluoromethane in the range independently from 9 mol-% to 19 mol-% where ethanol is present in the range from 1 mol-% to 10 mol-%.

In embodiments, the plant material used is kava (*Piper myristicum*). Multiple medicinal uses have been found for the active ingredients of kava (*Piper myristicum*), in particular achieving sedation and tranquilization in psychiatric and neurological disorders and treatment of insomnia and anxiety. See, for example, Volz, Hans-Peter, and M. Kieser. "Kava-kava extract WS 1490 versus placebo in anxiety disorders: A randomized placebo-controlled 25-week outpatient trial." *Pharmacopsychiatry* (1997). Sarris, J., D. J. Kavanagh, G. Byrne, K. M. Bone, J. Adams, and G. Deed. "The Kava Anxiety Depression Spectrum Study (KADSS): a randomized, placebo-controlled crossover trial using an aqueous extract of *Piper methysticum*." *Psychopharmacology* 205, no. 3 (2009): 399-407, which are incorporated herein by reference for all purposes. However, there have been reports of hepatotoxicity due to Kava [Clouatre, Dallas L. "Kava: examining new reports of toxicity." *Toxicology letters* 150, no. 1 (2004): 85-96, which is incorporated herein by reference for all purposes]; better extraction procedures could offer the promise of ameliorating these difficulties if only the active kavalactones, which account for much of the biological activity, could be extracted in a substantially purer form. The extracts obtained from kava are of utility of the treatment and amelioration of the disease process as well as the symptomatology of the diseases and pathological conditions.

In embodiments, the plant is *Piper methysticum* (Kava). In embodiments, the apparatus, method, or composition includes Freon™ 134a (1,1,1,2-Tetrafluoroethane). In embodiments, the apparatus, method, or composition includes Freon™ 134a (1,1,1,2-Tetrafluoroethane) and optionally one or more of carbon dioxide, nitrous oxide, sulfur hexafluoride, trifluoromethane, trifluoromethyl iodide, or tetrafluoromethane. In embodiments, the apparatus, method, or composition includes two extraction components (e.g., one component used in the extraction is Freon™ 134a (1,1,1,2-Tetrafluoroethane) and another is selected from the optional group of gases consisting of carbon dioxide, nitrous oxide, sulfur hexafluoride, trifluoromethane, trifluoromethyl iodide, or tetrafluoromethane; one component used in the extraction consists of Freon™

134a (1,1,1,2-Tetrafluoroethane) within the range of 20 mol-% to 99 mol-% and another is selected from the optional group of gases consisting of carbon dioxide, nitrous oxide, sulfur hexafluoride, trifluoromethane, trifluoromethyl iodide, or tetrafluoromethane in the range independently from 80 mol-% to 1 mol-%; one component used in the extraction is Freon™ 134a (1,1,1,2-Tetrafluoroethane) within the range of 80 mol-% to 90 mol-% and another is selected from the optional group of gases consisting of carbon dioxide, nitrous oxide, sulfur hexafluoride, trifluoromethane, trifluoromethyl iodide, or tetrafluoromethane in the range independently from 10 mol-% to 20 mol-%.

III. Examples

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

A problem in pharmaceutical chemistry relates to extraction of useful substances from plants or animals where such useful substances are employed for the formulation of a pharmaceutical or a nutraceutical. For example, morphine is a pharmaceutically highly useful material. All morphine used today originates in natural opium, which is obtained exclusively by extraction from *Papaver somniferum* (opium poppies). which is supplied primarily from India, Afghanistan, and Turkey where the poppies contain up to 20% of morphine in their latex. There are many total synthetic pathways to morphine but to date there is no reported synthesis of the alkaloid that would show much promise for a large-scale manufacturing [Zezula, Josef, and Tomas Hudlicky. "Recent progress in the synthesis of morphine alkaloids." Synlett 3 (2005): 388-405, which is incorporated herein by reference for all purposes]. Thus the supply of morphine remains dependent upon extraction of plant material.

Alternatively, the extracted useful substance may be employed as a synthetic intermediate in the manufacture of other drugs which are formulated as a pharmaceutical dosage form or a nutraceutical. As an example, thebaine is an opium alkaloid which is also extracted from opium poppies which itself is somewhat toxic and convulsant and when administered as a drug has no medical value. However, thebaine is used as the key intermediate for the synthesis of most of the non-natural opiates used in clinical practice. See, for example, Schiff, Paul L. "Opium and its alkaloids." American Journal of Pharmaceutical Education 66.2 (2002): 188-196; Tolstikova, T G. A V Bolkunov, E A Morozova, and S E Tolstikov. "Thebaine as a Precursor of Opioid Analgesic Agents." Chemistry for Sustainable Development 17 (2009) 109-126, which are incorporated herein by reference for all purposes.

Plants may be shrubs, trees, roots, berries, or other components of normal terrestrial plants, or they can be plants present in freshwater aquatic or marine environments. For examples of the latter, see Rocha, Fabiola Dutra, Angelica Ribeiro Soares, Peter John Houghton, Renato Crespo Pereira, Maria Auxiliadora Coelho Kaplan, and Valeria Laneuville Teixeira. "Potential cytotoxic activity of some Brazilian seaweeds on human melanoma cells." Phytotherapy Research 21, no. 2 (2007): 170-175, which is incorporated herein by reference for all purposes.

Although in many cases plants represent the major source of naturally occurring compounds which are useful in the prevention and treatment of diseases in humans and animals other natural sources can be important as a source of these materials. For example, many drugs have been derived from marine natural products [Jha, Rajeev Kumar, and Xu Zirong. "Biomedical compounds from marine organisms." Marine drugs 2.3 (2004): 123-146, which is incorporated herein by reference for all purposes].

Also, many marine drugs are extracted from organisms. See, for example, Thornburg, Christopher C., T. Mark Zabriskie, and Kerry L. McPhail. "Deep-Sea Hydrothermal Vents: Potential Hot Spots for Natural Products Discovery?" Journal of natural products 73, no. 3 (2010): 489-499, Pettit, George R., Jun-ping Xu, Zbigniew A. Cichacz, Michael D. Williams, Ann-Christine Dorsaz, Daniel C. Brune, Michael R. Boyd, and Ronald L. Cerny. "Antineoplastic agents 315. Isolation and structure of the marine sponge cancer cell growth inhibitor phakellistatin 5." Bioorganic & Medicinal Chemistry Letters 4, no. 17 (1994): 2091-2096; Yosief, Tesfamariam, Amira Rudi, and Yoel Kashman. "Asmarines A F, novel cytotoxic compounds from the marine sponge *Raspailia* species." Journal of natural products 63, no. 3 (2000): 299-304. Numata, Atsushi, Taro Amagata, Katsuhiko Minoura, and Tadayoshi Ito. "Gymnastatins, novel cytotoxic metabolites produced by a fungal strain from a sponge." Tetrahedron letters 38, no. 32 (1997): 5675-5678; Kobayashi, Jun'ichi, Shinji Takeuchi, Masami Ishibashi, Hideyuki Shigemori, and Takuma Sasaki. "Plakotenin, a new cytotoxic carboxylic acid from the okinawan marine sponge plakortis Sp." Tetrahedron letters 33, no. 18 (1992): 2579-2580.; Washida, Kazuto, Tomoyuki Koyama, Kaoru Yamada, Masaki Kita, and Daisuke Uemura. "Karatungiols A and B, two novel antimicrobial polyol compounds, from the symbiotic marine dinoflagellate *Amphidinium* sp." Tetrahedron letters 47, no. 15 (2006): 2521-2525, Kwon, Hak Cheol, Christopher A. Kauffman, Paul R. Jensen, and William Fenical. "Marinomycins A D, antitumor-antibiotics of a new structure class from a marine actinomycete of the recently discovered genus '*Marinispora*'." Journal of the American Chemical Society 128, no. 5 (2006): 1622-1632, which are incorporated herein by reference for all purposes. Drugs may extracted from many sources. See, for example, Yan, Yong-Ming, Jun Ai, Yan-Ni Shi, Zhi-Li Zuo, Bo Hou, Jie Luo, and Yong-Xian Cheng. "(±)-Aspongamide A, an N-Acetyldopamine Trimer Isolated from the Insect Aspongopus chinensis, Is an Inhibitor of p-Smad3." Organic letters 16, no. 2 (2014): 532-535, Whitehouse, M. W., A. G. Turner, C. K. C. Davis, and M. S. Roberts. "Emu oil (s): a source of non-toxic transdermal anti-inflammatory agents in aboriginal medicine." Inflammopharmacology 6, no. 1 (1998): 1-8, which are incorporated herein by reference for all purposes.

It should further be noted that typically natural products, including but not limited to marine natural products, and natural products from terrestrial plants, may contain multiple chiral centers which manifest optical activity. In general, this complicates the total synthesis of these natural products from commercially available achiral molecules. Although many methods exist in modern organic chemistry to perform enantioselective or chiral synthetic steps in high yield as well as to form multiple chiral centers in the correct stereochemical relation to each other in a single chemical step, many of these procedures are not well scalable from milligram scale in the laboratory to kilogram scale in production. Accordingly, semisynthesis is commonly employed. For example although there are many total syntheses of Paclitaxel, an important cancer drug, it is still produced from cells maintained in plant tissue culture derived from the pacific yew tree, *Taxus brevifolia* as none of the total syntheses are practical at large scale and there is not much possibility that they will ever be.

Many methods have been developed for extraction of natural products most particularly from plant, animal, fungi, bacteria, or viruses, where this has been historically important long before the advent of modern medicine in the preparation of materials required for the fragrance industry, such as the formulation of perfumes. These have been reviewed. See, for example, Wang, Lijun, and Curtis L. Weller. "Recent advances in extraction of nutraceuticals from plants." Trends in Food Science & Technology 17, no. 6 (2006): 300-312, which is incorporated herein by reference for all purposes. The oldest methods, which are still used, involve steam distillation, co-distillation with a solvent, typically ethanol, or Soxhlet extraction with an organic solvent. In these processes, the water, ethanol or organic solvent which co-distills with the desired mixture of natural products is removed, leaving the final product, typically as an oil, which may in its impure state may still be highly desired in the fragrance industry. For example Otto of roses is produced by steam distillation of rose (Rosa damascene) petals and is an important item of commerce in the perfume industry. However, steam distillation is an extremely inefficient and laborious process in practice, and it cannot be applied effectively to molecules which are somewhat polar in aqueous solution, as is, for example, the case with most alkaloids.

Extraction with organic solvents has been used for obtaining desired valuable substances from natural product plant, animal, fungi, bacteria, or virus material. This could involve Soxhlet extraction [De Castro, M D Luque, and F. Priego-Capote. "Soxhlet extraction: Past and present panacea." Journal of Chromatography A 1217, no. 16 (2010): 2383-2389, which is incorporated herein by reference for all purposes] whereby solvent is heated under reflux and the refluxed solvent is passed over a porous thimble containing the natural product. The natural product material is continually washed with fresh solvent in this approach, allowing the removal of much more product than would otherwise be possible because the amount in solution is not limited by equilibrium solubility of the solute in the solvent. While this approach is useful with highly soluble material, especially at the laboratory scale it becomes physically inefficient from the point of view of solvent and material handling at greater than a kilo scale. To some this can be addressed by using a different design, such as a fluidized bed extractor.

Extraction with hydrocarbon gases is also a useful technique, especially for the isolation of extremely hydrophobic materials such as waxes and oils [U.S. Pat. No. 5,405,633, Process for the extraction of fats and oils; European Patent Office Document EP0711508A1, Verfahren zur Extraktion von natürlichen Aromen aus fett-und ölhaltigen Naturstoffen; Nobre, Beatriz P., Luisa Gouveia, Patricia G S Matos, Ana F. Cristino, Antonio F. Palavra, and Rui L. Mendes. "Supercritical extraction of lycopene from tomato industrial wastes with ethane." Molecules 17, no. 7 (2012): 8397-8407]; which are incorporated herein by reference. Propane versus supercritical $CO_2$, is ten times more efficient at extracting carotenoids from pepper. See, for example, Daood, H. G., V. Illés, M. H. Gnayfeed, B. Mészáros, G. Horváth, and P. A. Biacs. "Extraction of pungent spice paprika by supercritical carbon dioxide and subcritical propane." The Journal of supercritical fluids 23, no. 2 (2002): 143-152, which is incorporated herein by reference for all purposes. However, these processes which employ ethane, propane, or butane although they can be worked safely still present a prima facie serious risk of fire or explosion, and great care must be taken on an industrial scale to avoid this. In "backyard" extraction of cannabis by this approach, many serious fires and explosions have occurred. See, for example, Downs, D. "Don't Try This At Home: Butane Hash Oil Penalties Stiffen", East Bay Express Aug. 11, 2015, which is incorporated herein by reference for all purposes. Also, although solvent extraction processes are used on a commercial scale, the extraction solvents which are currently used in these processes are not wholly satisfactory. Thus, when solvents such as hexane are used to extract aromatic oils, such as are used in the food and cosmetic industries, from plant matter containing those oils, unwanted materials contained in the plant, animal, fungi, bacteria, or virus, e.g. high molecular weight waxes, tend to be eluted along with the desired oil. This then can necessitate a further costly purification step [U.S. Pat. No. 2,467,403, Solvent extraction of castor oils, which is incorporated herein by reference for all purposes].

Halogenated solvents, such as dichloromethane or bromomethane, have been used for extraction of natural products [U.S. Pat. No. 2,294,811 Crystallized glucoside from red squill; U.S. Pat. No. 2,472,121, Decaffeinated soluble coffee; US 2010/0314240, Process of extracting aromatic compounds from plants using bromomethane as a solvent, which are incorporated herein by reference for all purposes]. By the use of a phase transfer catalyst even relatively polar alkaloids can be efficiently extracted [U.S. Pat. No. 4,818, 533, Production of high purity alkaloids, which is incorporated herein by reference for all purposes]. However, the use of these halogenated solvents has been diminished greatly in recent years for substances of pharmaceutical or nutraceutical activity due to concerns about solvent residues, even at the parts-per-million levels, in the final product, since these halogenated solvents are known to be toxic and some such as chloroform and bromomethane to be putative carcinogens.

More recently, steam distillation, co-distillation with a solvent, typically ethanol, or Soxhlet extraction have been substantially superseded except in "niche" applications by a method employing extraction with supercritical gases, most particularly supercritical carbon dioxide ($CO_2$). This method employs $CO_2$ under substantial temperature and pressure, typically greater than 200 atmospheres and at a temperature between 40° C. and 80° C. This has recently been reviewed. See, for example, De Melo, M. M. R., A. J. D. Silvestre, and C. M. Silva. "Supercritical fluid extraction of vegetable matrices: applications, trends and future perspectives of a convincing green technology." The Journal of Supercritical Fluids 92 (2014): 115-176, which is incorporated herein by reference for all purposes. Originally, this methodology was adopted on an industrial scale for decaffeination of coffee, when it was recognized that it was highly undesirable to utilize chlorinated solvents, such as dichloromethane, which leave trace solvent residues. See U.S. Pat. No. 2,472,121, Decaffeinated soluble coffee, which is incorporated herein by reference for all purposes. The methodology is described in U.S. Pat. No. 4,820,537 Method for decaffeinating coffee with a supercritical fluid; U.S. Pat. No. 5,288,511 Supercritical carbon dioxide decaffeination of acidified coffee, which are incorporated herein by reference for all purposes. The caffeine may be economically recovered [U.S. Pat. No.

4,996,317 Caffeine recovery from supercritical carbon dioxide, which is incorporated herein by reference for all purposes].

Though this approach has become widely used for extraction of plants, it suffers from a number of important deficiencies. In the first place, the temperatures and pressures which are required result in the need for specialized pressure vessels and high pressure pumps, and although such equipment is commercially available, is can become extremely expensive if a large scale (hundreds of kilograms of plant, animal, fungi, bacteria, or virus material per batch) is required. Since many natural products are present at concentrations in the plant, animal, fungi, bacteria, or virus which are relatively low, in many cases a few percent by weight or less, multiple large batches of raw plant, animal, fungi, bacteria, or virus material frequently need to be processed if a few to tens of kilo/day quantities of extract are required. In many cases, economic requirements dictate hundreds of kilos per day to be produced of extract in order for the extractive process to be run in a manner which is profitable. At this scale, supercritical $CO_2$ extraction becomes extremely expensive in terms of capital requirements for plant, animal, fungi, bacteria, or virus construction. Furthermore, because $CO_2$'s vapor pressure at room temperature is greater than sixty times normal atmospheric pressure, the use of $CO_2$ in a process creates a potential safety hazard relative to the same process operated at one atmosphere operation. Clearly, there is a need for processes which can be run in more conventional equipment at significantly lower pressures and temperatures.

Many extraction processes which are generically termed "supercritical" in nature with regard to $CO_2$ pressures and temperatures are actually not carried out at temperatures above the critical temperature and critical pressure of the gas, but are actually carried out at temperatures slightly to substantially below these pressures and temperatures. However, below the critical point temperature and pressure the efficiency of extraction of valuable natural products by $CO_2$ is markedly reduced. It is therefore commonly the case that so-called "supercritical" $CO_2$ extraction is not as efficient as would be the case if it were truly carried out under supercritical conditions. This limitation, which is not solely a semantic one, also contributes to a deficiency of the $CO_2$ extraction procedure which must be recognized. An advantage of $CO_2$ under subcritical conditions is that the solubility of undesired waxes is substantially lower at slightly reduced pressures [Jha, Sujit Kumar, and Giridhar Madras. "Modeling the solubilities of high molecular weight n-alkanes in supercritical carbon dioxide." Fluid phase equilibria 225 (2004): 59-62, which is incorporated herein by reference for all purposes].

It is generally recognized that liquid $CO_2$, regardless of whether it is used as the extracting fluid at fully supercritical conditions or at lower pressures and temperatures, is not a completely inert solvent. Carbon dioxide is relatively inert towards reactive compounds, but $CO_2$'s relative inertness should not be confused with complete inertness. For example, an attempt to conduct a hydrogenation in $CO_2$ over a platinum catalyst at 303 K will lead to the production of carbon monoxide CO, which itself could be quite reactive under the conditions of supercritical $CO_2$ extraction. Simple salts such as NaCl, KCl, and LiCl which are invariably present in plant material, especially if the said plant material has been heated, will serve efficiently to catalyze the addition of $CO_2$ to activated systems at one atmosphere. See, for example, Kihara, Nobuhiro, Nobutaka Hara, and Takeshi Endo. "Catalytic activity of various salts in the reaction of 2,3-epoxypropyl phenyl ether and carbon dioxide under atmospheric pressure." The Journal of Organic Chemistry 58, no. 23 (1993): 6198-6202, which is incorporated herein by reference for all purposes. Although it might be suggested that it is improbable that plant material would contain epoxides, this is not true as many terpenes will oxidize to produce epoxides; this could in fact be accelerated under supercritical $CO_2$ conditions if care is not taken to exclude $O_2$ from the system prior to pressurizing with $CO_2$. In the presence of simple inorganic catalysts such as zeolites, terpenes such as limonene are efficiently converted to epoxides by oxygen. See, for example, Bhattacharjee, Samiran, and James A. Anderson. "Epoxidation by Layered Double Hydroxide-Hosted Catalysts. Catalyst Synthesis and Use in the Epoxidation of R-(+)-Limonene and (−)-α-Pinene Using Molecular Oxygen." Catalysis letters 95, no. 3-4 (2004): 119-125, which is incorporated herein by reference for all purposes. Other materials that possess catalytic activity similar to the zeolites, such as clays, which could be present to some degree in plant material could serve as catalysts in a similar manner.

It should be however recognized that even a small amount of addition of $CO_2$ to a reactive moiety could result in multiple reactions under the conditions of supercritical extraction of a nature which would yield some amount of polymeric tarry material of indefinite character. Indeed, such tars do, to some degree, invariably occur in the course of supercritical $CO_2$ extraction. Supercritical $CO_2$ is, in fact, generally recognized as an excellent solvent in which to perform polymerization reactions [Kendall, Jonathan L., Dorian A. Canelas, Jennifer L. Young, and Joseph M. DeSimone. "Polymerizations in supercritical carbon dioxide." Chemical Reviews99, no. 2 (1999): 543-564, which is incorporated herein by reference for all purposes]. The presence of such tars and their removal represents a serious deficiency in supercritical $CO_2$ extraction of natural products, as commonly it is necessary to employ a secondary purification process following the extraction to remove them. Typically, this is realized by a method such as high vacuum fractional distillation, molecular distillation, or flash chromatography [Still, W. Clark, Michael Kahn, and Abhijit Mitra. "Rapid chromatographic technique for preparative separations with moderate resolution." The Journal of Organic Chemistry 43, no. 14 (1978): 2923-2925, which is incorporated herein by reference for all purposes]. These processes are expensive and furthermore result invariably in some measure of loss of the desired product. For example, aromatic oils contained in certain plants are complex substances containing a large number of individual compounds some of which are relatively volatile or relatively thermally unstable. Consequently, high distillation temperatures can tend to result in a loss of product either through evaporation of the more volatile compounds or thermal degradation of the more thermally unstable compounds. It would therefore be highly desirable to have a process which did not yield such undesired polymeric tarry materials.

Carbon dioxide will add to olefins at 1 atmosphere and 60° C. in the presence of a free radical initiator and a strong base; under conditions of elevated pressure this could be expected to occur in the presence of weaker bases (e.g. Potassium carbonates and hydroxides) which could be present in plant derived material, especially if it has been heated [Eghbali, Nicolas, and Chao-Jun Li. "Conversion of carbon dioxide and olefins into cyclic carbonates in water." Green Chem. 9, no. 3 (2007): 213-215, which is incorporated herein by reference for all purposes]. $CO_2$ will add to heterocyclic systems in the presence of catalytic amounts of copper halides at 1 atmospheres pressure and a temperature of 80° C. [Zhang, Liang, Jianhua Cheng, Takeshi Ohishi, and Zhaomin Hou. "Copper-Catalyzed Direct Carboxylation of C—H Bonds with Carbon Dioxide." Angewandte Chemie 122, no. 46 (2010): 8852-8855, which is incorporated herein by reference for all purposes].

All plant, animal, fungi, bacteria, or virus materials which serve as the raw feedstock for extraction contain a significant amount of water. Even if these materials are dried in vacuo, they nonetheless inherently possess some water which is only released at the elevated temperatures and pressures which are required to carry out the supercritical $CO_2$ extraction process. In completely pure $CO_2$, water has substantial solubility: at pressures and temperatures just below the critical point the mole fraction of water in $CO_2$ is about 0.02 [King Jr, Allen Dupree, and C. R. Coan. "Solubility of water in compressed carbon dioxide, nitrous oxide, and ethane. Evidence for hydration of carbon dioxide and nitrous oxide in the gas phase." Journal of the American Chemical Society 93, no. 8 (1971): 1857-1862, which is incorporated herein by reference for all purposes]. This paper further teaches that the water in the liquid $CO_2$ medium is almost completely solvated and is in the form of carbonic acid. Carbonic acid has a pKa of 3.45 [Adamczyk, Katrin, Mirabelle Prémont-Schwarz, Dina Pines, Ehud Pines, and Erik T J Nibbering. "Real-time observation of carbonic acid formation in aqueous solution." Science 326, no. 5960 (2009): 1690-1694, which is incorporated herein by reference for all purposes] and in a nonaqueous system such as liquid $CO_2$ it probably exists substantially in the form of the gas-phase dimer [Bernard, Jürgen, Markus Seidl, Ingrid Kohl, Klaus R. Liedl, Erwin Mayer, Óscar Gálvez, Hinrich Grothe, and Thomas Loerting. "Spectroscopic Observation of Matrix-Isolated Carbonic Acid Trapped from the Gas Phase." Angewandte Chemie International Edition 50, no. 8 (2011): 1939-1943, which is incorporated herein by reference for all purposes] in which it will effectively possess greater acidic character. Carbonic acid in this medium at elevated pressures and temperatures possesses substantial reactivity.

The critical pressure of $CO_2$ is significantly higher than that for alkanes or fluorocarbons. This anomalously high critical pressure is due to the fact that $CO_2$ has a high quadripole moment. It has been suggested that $CO_2$ may prove to be a solvent whose strength would rival or surpass that of alkanes and ketones. Because early models employed to calculate $CO_2$'s solvent power relied on a direct relationship between the Hildebrandt solubility parameter ($\delta$) and the square root of the critical pressure the solubility parameter of $CO_2$ was over-predicted by 20-100%, leading to early inflated claims as to its potential.

Supercritical $CO_2$ processes can benefit, in many cases, from the addition of various cosolvents. For example, addition of a few percent of methanol to $CO_2$ will result in dramatic increases in solubility of slightly polar materials, such as for example acridine [Brennecke, Joan F., and Charles A. Eckert. "Phase equilibria for supercritical fluid process design." AIChE Journal 35, no. 9 (1989): 1409-1427, which is incorporated herein by reference for all purposes]. The addition of a small amount of isopropanol to the supercritical $CO_2$ system has been carefully shown to dramatically increase the recovery of the sugar tagatose [Montañés, Fernando, Tiziana Fornari, Pedro J. Martín-Álvarez, Nieves Corzo, Agustin Olano, and Elena Ibáñez. "Selective recovery of tagatose from mixtures with galactose by direct extraction with supercritical $CO_2$ and different cosolvents." Journal of agricultural and food chemistry 54, no. 21 (2006): 8340-8345, which is incorporated herein by reference for all purposes]. While this approach is of principal utility with regard to the extraction of substances of intermediate hydrophobicity, it can be used, to advantage for very hydrophobic systems. For example, it has been reported that different very hydrophobic fractions containing useful antioxidant activity can be obtained from a bark extract by varying small amounts of ethanol which are added to the supercritical extraction [Braga, Mara E M, Rosa M S Santos, Ines J. Seabra, Roselaine Facanali, Marcia O M Marques, and Herminio C. de Sousa. "Fractioned SFE of antioxidants from maritime pine bark." The Journal of Supercritical Fluids 47, no. 1 (2008): 37-48, which is incorporated herein by reference for all purposes].

One approach to improvement of certain of the deficiencies of the supercritical $CO_2$ extraction system is to utilize a different supercritical gas. Unfortunately, many other gases have inconvenient critical properties. For example Argon has a critical pressure of 705 psi which can be attained easily but a critical temperature of only 151° K, which is so cold that it will not be a very effective solvent. Xenon would be an extremely good solvent but it is prohibitively expensive although but its critical pressure is high (847 psi) although its critical temperature is close to room temperature. Nitrous oxide is attractive because its critical temperature is just above room temperature (36° C.) although its critical pressure is rather high (1044 psi). Furthermore, nitrous oxide is potentially reactive to sensitive organic material in the presence of water, and the limited literature data suggest that it generally it is not as good a solvent in practice as $CO_2$.

Fluorocarbons are a chemical class selected from the field of fluorophilic compounds that are clear, colorless, odorless, nonflammable liquids that are essentially insoluble in water. In addition, fluorocarbon liquids are denser than water and soft tissue, have low surface tension and, for the most part, low viscosity.

Fluorocarbons have been used as solvents [U.S. Pat. Nos. 2,410,101, 2,449,671]. Chlorofluorocarbon Freon™ gases have been used in the extraction of perfume components [U.S. Pat. No. 3,150,050]. Chlorofluorocarbons have been used in the extraction of caffeine in coffee [U.S. Pat. No. 3,669,679]. However, this process employed a single class of fluorocarbon and no examples of mixtures of gases are therein cited.

Combinations of supercritical $CO_2$ and Freon™ solvents have been used for spice extraction of active materials [U.S. Pat. No. 4,490,398]. U.S. Pat. Nos. 6,455,087 and 6,649,205 also describe potential uses of fluorocarbons in solvent extraction methods.

Dielectric constant is not an important parameter in determining the interaction of hydrofluorocarbons and fluorocarbons in the extraction process and its sole use in the selection of cosolvents is not supported by the present scientific literature (see supra). For example, for fluoroethanes the Kamlet-Taft parameters, which do depend upon the dielectric constant, albeit not in a simple, monotonic manner, do not appear to be strongly predictive of the microscopic thermodynamic behavior of the system [Lagalante, Anthony F., Robert L. Hall, and Thomas J. Bruno. "Kamlet-Taft solvatochromic parameters of the sub- and supercritical fluorinated ethane solvents." The Journal of Physical Chemistry B 102, no. 34 (1998): 6601-6604, which is incorporated herein by reference for all purposes]. A much better choice of parameter would exemplified by one which is experimentally determined, such as the partial molal free energy of mixing. This parameter which can be readily measured [for example see Duce, Celia, Maria Tinè, L. Lepori, E. Matteoli, B. Marongiu, and Alessandra Piras. "A comparative study of thermodynamic properties of binary mixtures containing perfluoroalkanes." Journal of Thermal Analysis and Calorimetry 92, no. 1 (2008): 145-154, which is incorporated herein by reference for all purposes]. The second virial coefficients of the solution, which were measured in the work of Scott supra, or most localized energetic calculations of the mixtures using a mixed approach of Monte Carlo dynamics and Kohn-Sham quantum calculations (DFT) incorporating explicit electron correlation. These studies show that aggregation behavior of hydrofluorocarbons in fluorocarbon binary (or tertiary) mixtures represents the most important component of the prediction of solubility of hydrophobic organic compounds in these mixtures. A useful way to think of this is that the solution of a component in a fluorophilic mixture is controlled by the clustering of a component (typically a hydrofluorocarbon) around the solute on the dynamic timescale of order-disorder in the fluid system [as described in Gerig, John T. "Selective solvent interactions in a fluorous reaction system. "Journal of the American Chemical Society 127, no. 25 (2005): 9277-9284, which is incorporated herein by reference for all purposes]. This can also be approached experimentally [Binks, B. P., P. D. I. Fletcher, S. N. Kotsev, and R. L. Thompson. "Adsorption and aggregation of semifluorinated alkanes in binary and ternary mixtures with hydrocarbon and fluorocarbon solvents." Langmuir 13, no. 25 (1997): 6669-6682; Ruckenstein, E., and I. Shulgin. "Aggregation in binary solutions containing hexafluorobenzene." The Journal of Physical Chemistry B 103, no. 46 (1999): 10266-10271, which are incorporated herein by reference for all purposes] or spectroscopically, for example, with the use of small angle X-ray scattering [Brady, George W. "Cluster Formation in Perfluoroheptane-iso-Octane Systems near the Consolute Temperature." The Journal of Chemical Physics 32, no. 1 (1960): 45-51, which is incorporated herein by reference for all purposes], or even through surface tension measurements [McLure, I. A., B. Edmonds, and M. Lal. "Extremes in surface tension of fluorocarbon+hydrocarbon mixtures." Nature 241, no. 107 (1973): 71-71, which is incorporated herein by reference for all purposes]. Hydrogen bond donation is important, yet dielectric constant in a non-hydrogen bonding solvent has little to do with this critical parameter [Williams, Thomas D., Michael Jay, Hans-Joachim Lehmler, Michael E. Clark, Dennis J. Stalker, and Paul M. Bummer. "Solubility enhancement of phenol and phenol derivatives in perfluorooctyl bromide." Journal of pharmaceutical sciences 87, no. 12 (1998): 1585-1589, which is incorporated herein by reference for all purposes]. In a highly polar system as in water one can build a model for a dielectric constant based upon a hydrogen bound network [see for example Suresh, S. J., and V. M. Naik. "Hydrogen bond thermodynamic properties of water from dielectric constant data." The Journal of Chemical Physics 113, no. 21 (2000): 9727-9732, which is incorporated herein by reference for all purposes]. Using a classical approach [Oster, Gerald, and John G. Kirkwood. "The influence of hindered molecular rotation on the dielectric constants of water, alcohols, and other polar liquids." The Journal of Chemical Physics 11, no. 4 (1943): 175-178, which is incorporated herein by reference for all purposes]. Furthermore, the fact that $CO_2$ does not possess a dipole moment (although it has a quadripole moment) reinforces the lack of utility of the bulk dielectric constant as a metric within the context of the present invention.

While the processes described in the aforementioned documents are advantageous in some circumstances, there is a limit to the types of materials that can be extracted. Deficiencies are present in the use of steam, alcohols, supercritical or subcritical $CO_2$, or pure fluorocarbons to extracted valuable material from plant sources.

Surprisingly it has been found that mixtures of fluorocarbons and hydrofluorocarbons at or very close to the point where the two components are immiscible, although while still remaining partially or approximately miscible, but usually within a range of pressures and temperatures well below the critical temperature and pressure of the individual components, possess dramatically altered and improved solvent properties as compared with the individual components, if the mixtures are of a binary nature, or of binary mixtures of the individual components if the mixtures are of a ternary nature. [For example, see also Shin, Jungin, Moon Sam Shin, Won Bae, Youn-Woo Lee, and Hwayong Kim. "High-pressure phase behavior of carbon dioxide+ heptadecafluoro-1-decanol system." The Journal of Supercritical Fluids 44, no. 3 (2008): 260-265, Morgado, Pedro, Jana Black, J. Ben Lewis, Christopher R. Iacovella, Clare McCabe, Luis F G Martins, and Eduardo J M Filipe. "Viscosity of liquid systems involving hydrogenated and fluorinated substances: Liquid mixtures of (hexane+perfluorohexane)." Fluid Phase Equilibria 358 (2013): 161-165, which is incorporated herein by reference for all purposes.]

It has not previously been recognized that the extrema points of solutions of hydrofluorocarbons in fluorocarbons, and most particularly those hydrofluorocarbons and fluorocarbons under which the desired conditions of pressure and temperature result in a barely miscible system, would possess the unique ability to tunably extract, e.g. to extract in a manner which is tunable the desired hydrophobic organic materials from complex natural product mixtures. Described herein are processes, methods, and compositions related to discovery of extraction of natural products from plant material employing pure fluorocarbon liquids or gases and optionally admixtures of fluorocarbon and non-fluorocarbon gases and liquids. Extraction may be carried out in a highly selective manner such that specific components consisting of pure compounds or defined mixtures thereof may be extracted from said plant or animal material without extracting undesired materials.

Example 1

An extraction vessel is charged with 10 Kg. of *Cannabis Sativa* "trim". This material is obtained when harvesting cannabis flower, all the non-flower material which does not contain many trichomes is essentially a "waste product" from the production of the flower. It is most commonly the material which is used for cannabinoid extraction. This botanical material is contained in a cloth bag, which is placed within the extraction vessel in order to contain the material from dispersion through the extraction system. The vessel is evacuated. Subsequently, a premixed liquid phase which contains R-22 fluorocarbon (mole fraction 0.4), R-134a fluorocarbon (0.2 mole fraction) dimethyl ether (0.3 mole fraction), ethanol (0.05 mole fraction) and isobutane (0.05 mole fraction) is circulated through the plant material. The pressure is increased to 1.3 Mpa and the temperature to 45° C. and the circulation is continued for a 40-min period. At the end of this time, the liquid phase is pumped in the sealed system to a flash evaporator. The gases are removed and reprocessed through 3 A molecular sieves ($2/3K_2O.1/3Na_2O.Al_2O_3.2\ SiO_2.9/2\ H_2O$) and are compressed using a Corkin compressor into a storage vessel. The product oil from the flash evaporator is collected and assayed for cannabinoid content on an Agilent 1200 series HPLC with diode array detector Over a four-hour period while the extraction is carried out, the Freon™ turns bright green due to chlorophyll and other pigments which it contains that have been extracted from it. At the end of the four hour period, the Freon™ is compressed and recovered in a storage tank. It is regenerated by passing through a column of 4 A molecular sieves to remove water and terpenes which may be present.

The extracted material may be separated in the form of multiple components as a function of time during the extraction period. These multiple components contain different chemically distinct fractions, comprised of different approximate mixtures of compounds. Such mixtures may be precisely characterized in terms of composition and quantified in terms of concentration using analytical methodology well known to one normally skilled in the Art, such as Gas Chromatography, High Pressure Liquid Chromatography, Superfluid Critical Liquid Chromatography, Ultrahigh Resolution High Performance Liquid Chromatography, and the like. For the purposes of the present example the total amount of extracted material is quantified.

Data for Example 1.
Data:

| Run Number | Oil Recovered | % tetrahydrocannabinol |
|---|---|---|
| 1 | 1.72 kg | 68 |
| 2 | 2.02 | 66 |
| 3 | 1.98 | 82.3 |
| 4 | 2.18 | 71.5 |
| 5 | 2.26 | 71.3 |
| 6 | 1.92 | 64 |
| Mean | 2.01 | 70.5 |

Example 2

An extraction vessel is charged with 10 Kg. of *Cannabis Sativa* "trim". This material is obtained when harvesting cannabis flower, all the non-flower material which does not contain many trichomes is essentially a "waste product" from the production of the flower. It is most commonly the material which is used for cannabinoid extraction. This botanical material is contained in a cloth bag, which is placed within the extraction vessel in order to contain the material from dispersion through the extraction system. The vessel is evacuated. Subsequently, a premixed liquid phase which contains R-22 fluorocarbon (mole fraction 0.6), R-134a fluorocarbon (0.2 mole fraction), and dimethyl ether (0.2 mole fraction), is circulated through the plant material. The pressure is increased to 1.3 Mpa and the temperature to 45° C. and the circulation is continued for a 40-min period. At the end of this time, the liquid phase is pumped in the sealed system to a flash evaporator. The gases are removed and reprocessed through 3A molecular sieves ($2/3K_2O.1/3Na_2O.Al_2O_3.2\ SiO_2.9/2\ H_2O$) and are compressed using a Corkin compressor into a storage vessel. The product oil from the flash evaporator is collected and assayed for cannabinoid content on an Agilent 1200 series HPLC with diode array detector Over a four-hour period while the extraction is carried out, the Freon™ turns bright green due to chlorophyll and other pigments which it contains that have been extracted from it. At the end of the four hour period, the Freon™ is compressed and recovered in a storage tank. It is regenerated by passing through a column of 4 A molecular sieves to remove water and terpenes which may be present.

The extracted material may be separated in the form of multiple components as a function of time during the extraction period. These multiple components contain different chemically distinct fractions, comprised of different approximate mixtures of compounds. Such mixtures may be precisely characterized in terms of composition and quantified in terms of concentration using analytical methodology well known to one normally skilled in the Art, such as Gas Chromatography, High Pressure Liquid Chromatography, Superfluid Critical Liquid Chromatography, Ultrahigh Resolution High Performance Liquid Chromatography, and the like. For the purposes of the present example the total amount of extracted material is quantified.

| Run Number | Oil Recovered | % tetrahydrocannabinol |
|---|---|---|
| 1 | 2.2 Kg | 68 |
| 2 | 2.4 | 72 |
| 3 | 2.1 | 76 |
| 4 | 2.0 | 62 |
| Mean | 2.175 Kg | 69.5 |

Example 3

An extraction vessel is charged with about 50 Kg. of *Cannabis Sativa* "trim". This material is obtained when harvesting cannabis flower, all the non-flower material which does not contain many trichomes is essentially a "waste product" from the production of the flower. It is most commonly the material which is used for cannabinoid extraction. This botanical material is contained in a cloth bag, which is placed within the extraction vessel in order to contain the material from dispersion through the extraction system. The vessel is evacuated. Subsequently, a premixed liquid phase which contains R-22 fluorocarbon (mole fraction 0.4), R-134a fluorocarbon (0.2 mole fraction) dimethyl ether (0.3 mole fraction), ethanol (0.05 mole fraction) and isobutane (0.05 mole fraction) is circulated through the plant material. The pressure is increased to 1.3 Mpa and the temperature to 45° C. and the circulation is continued for a 40-min period. At the end of this time, the liquid phase is pumped in the sealed system to a flash evaporator. The gases are removed and reprocessed through 3 A molecular sieves ($2/3K_2O.1/3Na_2O.Al_2O_3.2\ SiO_2.9/2\ H_2O$) and are compressed using a Corkin compressor into a storage vessel. The product oil from the flash evaporator is collected and assayed for cannabinoid content on an Agilent 1200 series HPLC with diode array detector Over a four-hour period while the extraction is carried out, the Freon™ turns bright green due to chlorophyll and other pigments which it contains that have been extracted from it. At the end of the four hour period, the gases is compressed and recovered in a storage tank. It is regenerated by passing through a column of 3 A molecular sieves to remove water and terpenes which may be present.

The extracted material may be separated in the form of multiple components as a function of time during the extraction period. These multiple components contain different chemically distinct fractions, comprised of different approximate mixtures of compounds. Such mixtures may be precisely characterized in terms of composition and quantified in terms of concentration using analytical methodology well known to one normally skilled in the Art, such as Gas Chromatography, High Pressure Liquid Chromatography, Superfluid Critical Liquid Chromatography, Ultrahigh Resolution High Performance Liquid Chromatography, and the like. For the purposes of the present example the total amount of extracted material is quantified.

Run 1
Charge: 48.72 Kg
Extraction yields 7.82 Kg of oil, 68% by weight total cannabinoids
Run 2
Extraction yields 779 Kg of oil, 72% cannabinoids by weight Example 4

An extraction vessel is charged with 10 Kg. of *Cannabis Sativa* "flower". This botanical material is contained in a cloth bag, which is placed within the extraction vessel in order to contain the material from dispersion through the extraction system. The vessel is evacuated. Subsequently, a premixed liquid phase which contains R-22 fluorocarbon (mole fraction 0.4), R-134a fluorocarbon (0.2 mole fraction) dimethyl ether (0.3 mole fraction), ethanol (0.05 mole fraction) and isobutane (0.05 mole fraction) is circulated through the plant material. The pressure is increased to 1.3 Mpa and the temperature to 45° C. and the circulation is continued for a 40-min period. At the end of this time, the liquid phase is pumped in the sealed system to a flash evaporator. The gases are removed and reprocessed through 3 A molecular sieves ($2/3K_2O.1/3Na_2O.Al_2O_3.2$ $SiO_2.9/2$ $H_2O$) and are compressed using a Corkin compressor into a storage vessel. The product oil from the flash evaporator is collected and assayed for cannabinoid content on an Agilent 1200 series HPLC with diode array detector Over a four-hour period while the extraction is carried out, the Freon™ turns bright green due to chlorophyll and other pigments which it contains that have been extracted from it. At the end of the four hour period, the gases is compressed and recovered in a storage tank. It is regenerated by passing through a column of 3 A molecular sieves to remove water and terpenes which may be present.

The extracted material may be separated in the form of multiple components as a function of time during the extraction period. These multiple components contain different chemically distinct fractions, comprised of different approximate mixtures of compounds. Such mixtures may be precisely characterized in terms of composition and quantified in terms of concentration using analytical methodology well known to one normally skilled in the Art, such as Gas Chromatography, High Pressure Liquid Chromatography, Superfluid Critical Liquid Chromatography, Ultrahigh Resolution High Performance Liquid Chromatography, and the like. For the purposes of the present example the total amount of extracted material is quantified.

Run 1: 2.4 Kg of oil, 78% cannabinoids
Run 2: 2.2 Kg of oil, 82% cannabinoids
Run3: 2.6 Kg of oil, 79% cannabinoids Example 5

A stainless steel tube about 10" in length and 1.25" in diameter was equipped with sanitary flanges at each end, to which could be affixed a pressure transducer and a sight glass. A sample of amount 500 mg to 5 gm was placed in the tube contained in an inert polypropylene mesh bag. The entire apparatus was placed on a toploading balance, and by means of a flexible hose gases could be added to the vessel. By means of the change in weight, different gases could be added in known ratios. The apparatus, after filling, could then be maintained in a constant temperature bath for any desired period of time, and at the end of this time the apparatus could be opened, the bag removed and the gas volatilized, and the extracted residue dissolved in a suitable solvent (generally acetone) in a quantitative manner. The acetone could then be transferred to a tared roundbottom flask, and solvent removed on a rotary evaporator under vacuum. The amount of the residue in the flask corresponds to the total soluble mass extracted, and this is then quantified by weighing the flask. After determining this weight, the gummy residue could be redissolved in a suitable solvent (generally methanol) in a volumetric flask and aliquots of this material analyzed by HPLC to determine the amounts of cannabinoids (eg. THC, CBD, THCA, and so forth). HPLC analysis is carried out using an Agilent 1100 Series Separation Module, with an Agilent diode array detector, using Agilent Chemstation Software. The column used is a Restek Raptor ARC-18 2.7 μm, 4.6×150 mm column, equipped with a Guard Cartridge (Restek Catalog #9304A0252) or equivalent). Samples are injected and eluted with an isocratic solvent system A/B (25/75). Mobile phase A consists of 0.1% Trifluoroacetic acid (TFA) in $H_2O$ (chromatography quality). Mobile phase B consists of 0.1% TFA in chromatography grade acetonitrile. The Detector Wavelength is 220 nm, Flow Rate is 1.5 mL/min, Injection Volume is 10 and Column Temp is 45.0° C. Under these conditions the Run time is about 9 minutes. Typically, a standards calibration curve of THC of nine concentrations (5-200 ppm) is run daily.

Using these conditions, the efficiency of mixtures of fluorocarbon R22 and dimethyl ether (DME) to extract total cannabinoids in a single 30-minute extraction at 26° C. is shown in FIG. 1.

Figure 2:
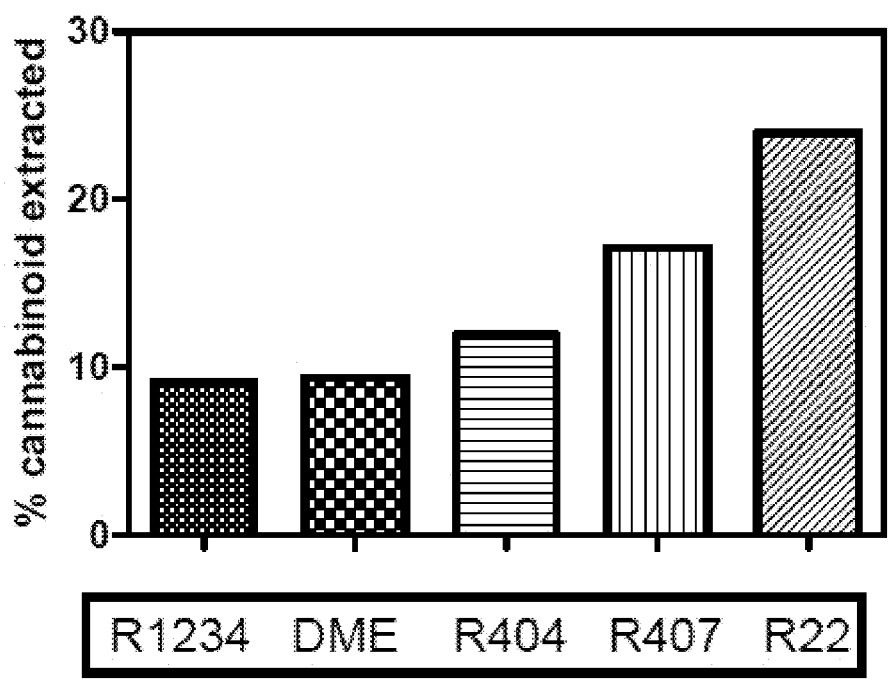
FIG. 2 Graph demonstrating that the efficiency of pure materials to extract cannabinoids in a single 30-minute procedure at 26° C. can be determined.

Using the same approach, the efficiency of the pure materials to extract cannabinoids in a single 30-minute procedure at 26° C. can be determined and this is shown in FIG. 2.

Embodiments

Embodiments contemplated herein include the following.

Embodiment 1

A method of extracting a natural organic compound from a natural material, said method comprising contacting said natural material with an extraction fluid thereby extracting said natural organic compound from said natural material into said extraction fluid to from an extracted fluid solution, wherein said extraction fluid comprises a fluorophilic compound and a hydrofluorocarbon.

Embodiment 2

The method of embodiment 1, wherein said extraction fluid is a non-ideal fluid.

Embodiment 3

The method of embodiments 1 or 2, wherein the natural material is a material derived from a plant, an animal, a fungi, a bacteria or a virus.

Embodiment 4

The method of embodiments 1 or 2, wherein the natural material is a material derived from a plant.

Embodiment 5

The method of embodiments 1 or 2, wherein the plant is *Piper methysticum, Cannabis* spp., *Salvia* spp., *Banisteriopsis caapi, Psychotria viridis* (chacruna), *Diplopterys cabrerana, Peganum harmala, Humulus lupulus* or mixture thereof.

Embodiment 6

The method of embodiments 1 or 2, wherein the plant is *Cannabis Sativa*.

Embodiment 7

The method of one of embodiments 1 to 6, wherein the natural organic compound is a biologically active organic compound.

Embodiment 8

The method of one of embodiments 1 to 6, wherein the natural organic compound is an aromatic compound.

Embodiment 9

The method of one of embodiments 1 to 6, wherein the natural organic compound forms art of an aromatic oil or essential oil.

Embodiment 10

The method of one of embodiments 1 to 6, wherein the natural organic compound is caffeine.

Embodiment 11

The method of one of embodiments 1 to 6, wherein the natural organic compound is a terpene, a humulone, a lupulone, a myrcene, a humulene, a caryophyllene, an alkaloid, a flavonoid, a cannabinoid, menthol, capsaicin, anise or camphor.

Embodiment 12

The method of one of embodiments 1 to 6, wherein the natural organic compound is xanthohumol, 8-prenylnaringenin or isoxanthohumol.

Embodiment 13

The method of one of embodiments 1 to 6, wherein the natural organic compound is a prenylflavonoid.

Embodiment 14

The method of one of embodiments 1 to 6, wherein the natural organic compound is a kavalactone or a salvorin.

Embodiment 15

The method of one of embodiments 1 to 6, wherein the natural organic compound is a cannibinoid.

Embodiment 16

The method of one of embodiments 1 to 6, wherein the natural organic compound is tetrahydrocannabinol, cannabidiol or cannabinol.

Embodiment 17

The method of one of embodiments 1 to 6, wherein the natural organic compound is tetrahydrocannabinol.

Embodiment 18

The method of one of embodiments 1 to 17, wherein at least 5,000 g of said natural organic compound is present in said extracted fluid solution.

Embodiment 19

The method of one of embodiments 1 to 18, wherein said extraction fluid does not comprise supercritical CO2.

Embodiment 20

The method of one of embodiments 1 to 18, wherein said extraction fluid does not comprise argon.

Embodiment 21

The method of one of embodiments 1 to 18, wherein said extraction fluid does not comprise xenon.

Embodiment 22

The method of one of embodiments 1 to 18, wherein said extraction fluid does not comprise nitrous oxide.

Embodiment 23

The method of one of embodiments 1 to 22, wherein said extraction fluid further comprises trifluorethanol or hexafluoroisopropanol.

Embodiment 24

The method of one of embodiments 1 to 23, wherein said extraction fluid is above about 15° C.

Embodiment 25

The method of one of embodiments 1 to 23, wherein said extraction fluid is above about 20° C.

Embodiment 26

The method of one of embodiments 1 to 23, wherein said extraction fluid is from about 15° C. to about 35° C.

Embodiment 27

The method of one of embodiments 1 to 23, wherein said extraction fluid is from about 20° C. to about 30° C.

Embodiment 28

The method of one of embodiments 1 to 27, wherein the hydrofluorocarbon is a hydrofluoroether, a hydrofluoroketone, a hydrofluoroaromatic or a hydrofluoroolefin.

Embodiment 29

The method of one of embodiments 1 to 27, wherein the hydrofluorocarbon is chlorodifluoromethane, methyl nonafluoroisobutyl ether, methyl nonafluorobutyl ether, ethyl nonafluoroisobutyl ether, ethyl nonafluorobutyl ether, 3-ethoxy-1,1,1,2,3,4,4,5,5,6,6,6-dodecafluoro-2-trifluoromethylhexane.trifluoromethane (HFC-23), difluoromethane (HFC-32), pentafluoroethane (HFC-125), 1,1,2,2-tetrafluoroethane (HFC-134), 1,1,1,2-tetrafluoroethane (HFC-134a), 1,1,1-trifluoroethane (HFC-143a), 1,1-difluoroethane (HFC-152a) or fluoroethane (HFC-161).

Embodiment 30

The method of one of embodiments 1 to 29, wherein the fluorophilic compound is dimethyl ether.

Embodiment 31

The method of one of embodiments 1 to 30, wherein the extraction fluid is a liquid-gas mixture fluid.

Embodiment 32

The method of one of embodiments 1 to 31, further comprising, prior to said contacting, freezing the natural material at a temperature from about 0° C. to about −60° C.

Embodiment 33

The method of one of embodiments 1 to 32, wherein the mole fraction of the fluorophilic compound is at least four-fold greater than the mole fraction of the hydrofluorocarbon.

Embodiment 34

The method of one of embodiments 1 to 33, further comprising separating said extraction fluid from said natural material by volatizing said extraction fluid to form a volatilized extraction fluid.

Embodiment 35

The method of embodiment 34, further comprising chilling and compressing the volatilized extraction fluid to form a liquid extraction fluid.

Embodiment 36

The method of embodiments 34 or 35, further comprising recirculating the liquid extraction fluid to the natural material.

Embodiment 37

The method of one of embodiments 34 to 36, further comprising collecting separated fractions of the liquid extraction fluid.

Embodiment 38

A fluid comprising chlorodifluoromethane and dimethylether.

Embodiment 39

The fluid of embodiment 38, wherein said fluid is a non-ideal fluid.

Embodiment P1

A process for extraction of natural products of medicinal, pharmacological, or other value from plant, animal, fungi, bacteria, or virus mixtures consisting of
(a) freezing the plant, animal, fungi, bacteria, or virus material to a temperature between 0° C. and −60° C. by the use of a blast freezer or a compressed cryogenic gas
(b) passing a fluid over the plant, animal, fungi, bacteria, or virus material with the use of a recirculating pump, whereby the fluid consists of three components:
  (i) a fluorophilic compound
  (ii) a hydro fluorocarbon
  (iii) a third component which is a fluorophilic amine, alcohol, or nonfluorinated alkanol
  (iv) wherein the mole fraction of the fluorocarbon is at least four-fold greater than the mole fraction of the hydrofluorocarbon, and the mole fraction of the third component is four-fold less than the hydrofluorocarbon
(c) volatizing the fluorophilic compound which has been passed over the plant, animal, fungi, bacteria, or virus material using a heated column, whereby the extracted plant, animal, fungi, bacteria, or virus material solubilized by the fluid remains at the bottom of the said column and the fluorophilic compound is extracted in a gaseous form at one end of said column
(d) chilling the volatilized fluorophilic compound with a heat exchanger and compressing the fluorophilic compound to the liquid state
(e) warming the liquefied fluorophilic compound in a controlled manner
(f) recirculating the liquefied warm fluorophilic compound back through the plant, animal, fungi, bacteria, or virus material in a continuous manner
(g) slowly increasing the temperature of the liquefied recirculated fluorophilic compound which flows back over the plant, animal, fungi, bacteria, or virus material, thereby increasing the temperature of the said plant, animal, fungi, bacteria, or virus material from the temperature range of freezing to a temperature range between 40° C. and 80° C.
(h) collecting separated fractions at the bottom of the volatilizing column as the temperature is thereby increased.

Embodiment P2

A process according to embodiment P1, wherein said fluorocarbon is 1,1,1,2 tetrafluoroethane.

Embodiment P3

A process according to embodiment P1, wherein said fluorocarbon is tetrafluoromethane.

Embodiment P4

A process according to embodiment P1, wherein said fluorocarbon is hexafluoroethane.

Embodiment P5

A process according to embodiment P1, wherein said fluorocarbon is trifluoromethyl iodide.

Embodiment P6

A process according to embodiment P1, wherein said fluorocarbon is perfluorocyclobutane.

Embodiment P7

A process according to embodiment P1, wherein said fluorocarbon is perfluorotributylamine.

Embodiment P8

A process according to embodiment P1, wherein said fluorocarbon is perfluoro-n-propane.

Embodiment P9

A process for extraction of natural products of medicinal, pharmacological, or other value from plant, animal, fungi, bacteria, or virus mixtures consisting of
- (a) freezing the plant, animal, fungi, bacteria, or virus material to a temperature between 0° C. and −60° C. by the use of a blast freezer or a compressed cryogenic gas
- (b) passing a fluid over the plant, animal, fungi, bacteria, or virus material with the use of a recirculating pump, whereby the fluid consists of three components:
  - (v) a fluorophilic compound
  - (vi) a hydrofluorocarbon
  - (vii) a third component which is an inert gas
- (c) volatilizing the fluorophilic compound which has been passed over the plant, animal, fungi, bacteria, or virus material using a heated column, whereby the extracted plant, animal, fungi, bacteria, or virus material solubilized by the fluid remains at the bottom of the said column and the fluorophilic compound is extracted in a gaseous form at one end of said column
- (d) chilling the volatilized fluorophilic compound with a heat exchanger and compressing the fluorophilic compound to the liquid state
- (e) warming the liquefied fluorophilic compound in a controlled manner
- (f) recirculating the liquefied warm fluorophilic compound back through the plant, animal, fungi, bacteria, or virus material in a continuous manner
- (g) slowly increasing the temperature of the liquefied recirculated fluorophilic compound which flows back over the plant, animal, fungi, bacteria, or virus material, thereby increasing the temperature of the said plant, animal, fungi, bacteria, or virus material from the temperature range of freezing to a temperature range between 40° C. and 80° C.
- (h) collecting separated fractions at the bottom of the volatilizing column as the temperature is thereby increased.

Embodiment P10

A process according to embodiment P9, wherein said fluorocarbon is 1,1,1,2 tetrafluoroethane and the inert gas is $SF_6$.

Embodiment P11

A process according to embodiment P9, wherein said fluorocarbon is 1,1,1,2 tetrafluoroethane and the inert gas is $CO_2$.

Embodiment P12

A process according to embodiment P9, wherein said fluorocarbon is 1,1,1,2 tetrafluoroethane and the inert gas is $N_2O$.

Embodiment P13

A process according to embodiment P9, wherein said fluorocarbon is 1,1,1,2 tetrafluoroethane and the inert gas is $CH_4$.

Embodiment P14

A process according to embodiment P9, wherein said fluorocarbon is 1,1,1,2 tetrafluoroethane and the inert gas is $C_2H_6$.

Embodiment P15

A process according to embodiment P9, wherein said fluorocarbon is tetrafluoromethane and the inert gas is $SF_6$.

Embodiment P16

A process according to embodiment P9, wherein said fluorocarbon is tetrafluoromethane and the inert gas is $CO_2$.

Embodiment P17

A process according to embodiment P9, wherein said fluorocarbon is tetrafluoromethane and the inert gas is $N_2O$.

Embodiment P18

A process according to embodiment P9, wherein said fluorocarbon is tetrafluoromethane and the inert gas is $CH_4$.

Embodiment P19

A process according to embodiment P9, wherein said fluorocarbon is tetrafluoromethane and the inert gas is $C_2H_6$.

Embodiment P20

A process according to embodiment P9, wherein said fluorocarbon is perfluorocyclobutane and the inert gas is $SF_6$.

Embodiment P21

A process according to embodiment P9, wherein said fluorocarbon is perfluorocyclobutane and the inert gas is $CO_2$.

Embodiment P22

A process according to embodiment P9, wherein said fluorocarbon is perfluorocyclobutane and the inert gas is $N_2O$.

Embodiment P23

A process according to embodiment P9, wherein said fluorocarbon is perfluorocyclobutane and the inert gas is $CH_4$.

Embodiment P24

A process according to embodiment P9, wherein said fluorocarbon is perfluorocyclobutane and the inert gas is $C_2H_6$.

Embodiment P25

A process for extraction of natural products of medicinal, pharmacological, or other value from plant, animal, fungi, bacteria, or virus mixtures consisting of
  (a) freezing the plant, animal, fungi, bacteria, or virus material to a temperature between 0° C. and −60° C. by the use of a blast freezer or a compressed cryogenic gas
  (b) passing a fluid over the plant, animal, fungi, bacteria, or virus material with the use of a recirculating pump, whereby the fluid consists of three components:
    (i) a fluorophilic compound
    (ii) a hydrofluorocarbon
    (iii) an ionic liquid
  (c) volatilizing the fluorophilic compound which has been passed over the plant, animal, fungi, bacteria, or virus material using a heated column, whereby the extracted plant, animal, fungi, bacteria, or virus material solubilized by the fluid remains at the bottom of the said column and the fluorophilic compound is extracted in a gaseous form at the top of said column
  (d) chilling the volatilized fluorophilic compound with a heat exchanger and compressing the fluorophilic compound to the liquid state
  (e) warming the liquefied fluorophilic compound in a controlled manner
  (f) recirculating the liquefied warm fluorophilic compound back through the plant, animal, fungi, bacteria, or virus material in a continuous manner
  (g) slowly increasing the temperature of the liquefied recirculated fluorophilic compound which flows back over the plant, animal, fungi, bacteria, or virus material, thereby increasing the temperature of the said plant, animal, fungi, bacteria, or virus material from the temperature range of freezing to a temperature range between 40° C. and 80° C.
  (h) collecting separated fractions at the bottom of the volatilizing column as the temperature is thereby increased.

What is claimed is:

1. A method of extracting a natural organic compound from a natural material, said method comprising contacting said natural material with an extraction fluid thereby extracting said natural organic compound from said natural material into said extraction fluid to form an extracted fluid solution, wherein said extraction fluid comprises a fluorophilic compound and a hydrofluorocarbon,
  wherein said extraction fluid further comprises trifluoroethanol or hexafluoroisopropanol.

2. The method of claim 1, wherein the natural material is a material derived from a plant, an animal, a fungi, a bacteria or a virus.

3. The method of claim 2, wherein the plant is *Piper methysticum, Cannabis* spp., *Salvia* spp., *Banisteriopsis caapi, Psychotria viridis* (*chacruna*), *Diplopterys cabrerana, Peganum harmala, Humulus lupulus* or mixture thereof.

4. The method of claim 2, wherein the plant is *Cannabis Sativa*.

5. The method of claim 1, wherein the natural organic compound is a biologically active organic compound, an aromatic compound, or forms part of an aromatic oil or essential oil.

6. The method of claim 1, wherein the natural organic compound is caffeine, a terpene, a humulone, a lupulone, a myrcene, a humulene, a caryophyllene, an alkaloid, a flavonoid, a cannabinoid, menthol, capsaicin, anise, camphor, xanthohumol, 8-prenylnaringenin, isoxanthohumol, a prenylflavonoid, a kavalactone, a salvorin, a cannabinoid, tetrahydrocannabinol, cannabidiol, or cannabinol.

7. The method of claim 1, wherein at least 5000 g of said natural organic compound is present in said extracted fluid solution.

8. The method of claim 1, wherein said extraction fluid does not comprise supercritical $CO_2$.

9. The method of claim 1, wherein said extraction fluid does not comprise argon, xenon, or nitrous oxide.

10. The method of claim 1, wherein said extraction fluid is above about 15° C.

11. The method of claim 1, wherein the hydrofluorocarbon is a hydrofluoroether, a hydrofluoroketone, a hydrofluoroaromatic or a hydrofluoroolefin.

12. The method of claim 1, wherein the hydrofluorocarbon is chlorodifluoromethane, methyl nonafluoroisobutyl ether, methyl nonafluorobutyl ether, ethyl nonafluoroisobutyl ether, ethyl nonafluorobutyl ether, 3-ethoxy-1, 1,1,2,3,4, 4,5, 5,6,6,6-dodecafluoro-2-trifluoromethylhexane.trifluoromethane (HFC-23), difluoromethane (HFC-32), pentafluoroethane (HFC-125), 1,1,2,2-tetrafluoroethane (HFC-134), 1,1,1,2-tetrafluoroethane (HFC-134a), 1,1,1-trifluoroethane (HFC-143a), 1,1-difluoroethane (HFC-152a), (1,1,1,3,3,3-hexafluoro-2-(fluoromethoxy)propane, 1,2,2,2-tetrafluoroethyl difluoromethyl ether, 2-chloro-1,1,2,-trifluoroethyl difluoromethyl ether, l-chloro-2,2,2-trifluoroethyl difluoromethyl ether, 2,2-dichloro-1,1-difluoromethyl ether, or fluoroethane (HFC-161).

13. The method of claim 1, wherein the fluorophilic compound is dimethyl ether, methyl ethyl ether, methyl methyl n-propyl ether, methyl isopropyl ether, methyl-n-butyl ether, diethyl ether, methyl tert-butyl ether, or ethyl tert-butyl ether.

14. The method of claim 1, further comprising, prior to said contacting, freezing the natural material at a temperature from about 0° C. to about −60° C.

15. The method of claim 1, wherein the mole fraction of the fluorophilic compound is at least four-fold greater than the mole fraction of the hydrofluorocarbon.

16. The method of claim 1, further comprising separating said extraction fluid solution into an isolated natural organic compound and a separated extraction fluid.

17. The method of claim 16, further comprising chilling and compressing the volatilized extraction fluid to form a liquid extraction fluid.

18. The method of claim 16, further comprising recirculating the liquid extraction fluid to the natural material.

19. A method of extracting a natural organic compound from a natural material, said method comprising contacting said natural material with an extraction fluid thereby extracting said natural organic compound from said natural material into said extraction fluid to form an extracted fluid solution, wherein said extraction fluid comprises a fluorophilic compound and a hydrofluorocarbon, wherein the hydrofluorocarbon is a hydrofluoroether, a hydrofluoroketone, a hydrofluoroaromatic or a hydrofluoroolefin.

20. The method of claim 19, wherein the natural material is a material derived from a plant, an animal, a fungi, a bacteria or a virus.

21. The method of claim 20, wherein the plant is *Piper methysticum, Cannabis* spp., *Banisteriopsis caapi, Psychotria viridis* (*chacruna*), *Diplopterys cabrerana, Peganum harmala, Humulus lupulus* or mixture thereof.

22. The method of claim 19, wherein the natural organic compound is caffeine, a terpene, a humulone, a lupulone, a myrcene, a humulene, a caryophyllene, an alkaloid, a flavonoid, a cannabinoid, menthol, capsaicin, anise, camphor, xanthohumol, 8-prenylnaringenin, isoxanthohumol, a prenylflavonoid, a kavalactone, a salvorin, a cannabinoid, tetrahydrocannabinol, cannabidiol, or cannabinol.

23. The method of claim 19, further comprising recirculating the liquid extraction fluid to the natural material.

24. The method of claim 19, further comprising chilling and compressing the volatilized extraction fluid to form a liquid extraction fluid.

25. The method of claim 19, wherein the fluorophilic compound is dimethyl ether, methyl ethyl ether, methyl n-propyl ether, methyl isopropyl ether, methyl-n-butyl ether, diethyl ether, methyl tert-butyl ether, or ethyl tert-butyl ether.

26. The method of claim 19, further comprising, prior to said contacting, freezing the natural material at a temperature from about 0° C. to about −60° C.

27. The method of claim 19, further comprising separating said extraction fluid solution through volatilization to form an isolated natural material and a volatilized extraction fluid.

28. The method of claim 19, wherein said extraction fluid further comprises trifluoroethanol or hexafluoroisopropanol.

\* \* \* \* \*